United States Patent
Snider et al.

(10) Patent No.: US 10,928,393 B2
(45) Date of Patent: *Feb. 23, 2021

(54) METHODS OF TREATING CARDIOVASCULAR DISEASES AND PREDICTING THE EFFICACY OF EXERCISE THERAPY

(71) Applicant: Critical Care Diagnostics, Inc., San Diego, CA (US)

(72) Inventors: James V. Snider, San Diego, CA (US); Robert W. Gerwien, Newington, CT (US)

(73) Assignee: Critical Care Diagnostics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/170,870

(22) Filed: Oct. 25, 2018

(65) Prior Publication Data

US 2019/0049444 A1 Feb. 14, 2019

Related U.S. Application Data

(63) Continuation of application No. 15/409,283, filed on Jan. 18, 2017, now abandoned, which is a continuation of application No. 14/299,851, filed on Jun. 9, 2014, now Pat. No. 9,551,708, which is a continuation of application No. 13/552,533, filed on Jul. 18, 2012, now Pat. No. 8,748,110.

(60) Provisional application No. 61/508,923, filed on Jul. 18, 2011, provisional application No. 61/509,359, filed on Jul. 19, 2011.

(51) Int. Cl.

| | |
|---|---|
| *G01N 33/53* | (2006.01) |
| *G01N 33/68* | (2006.01) |
| *A61P 9/04* | (2006.01) |
| *G01N 33/566* | (2006.01) |
| *C07K 14/705* | (2006.01) |
| *C07K 14/715* | (2006.01) |
| *C07K 14/54* | (2006.01) |
| *C07K 16/24* | (2006.01) |
| *C07K 16/28* | (2006.01) |

(52) U.S. Cl.
CPC .............. *G01N 33/566* (2013.01); *A61P 9/04* (2018.01); *G01N 33/53* (2013.01); *G01N 33/6869* (2013.01); *G01N 33/6893* (2013.01); *C07K 14/54* (2013.01); *C07K 14/7155* (2013.01); *C07K 16/2866* (2013.01); *G01N 2333/7155* (2013.01); *G01N 2800/32* (2013.01); *G01N 2800/52* (2013.01)

(58) Field of Classification Search
None
See application file for complete search history.

(56) References Cited

U.S. PATENT DOCUMENTS

| | | |
|---|---|---|
| 7,432,060 B2 | 10/2008 | Lee |
| 7,655,415 B2 | 2/2010 | Lee |
| 7,670,769 B2 | 3/2010 | Lee |
| 7,985,558 B2 | 7/2011 | Lee |
| 7,989,210 B2 | 8/2011 | Lee |
| 7,998,683 B2 | 8/2011 | Snider et al. |
| 8,090,562 B2 | 1/2012 | Snider et al. |
| 8,420,785 B2 | 4/2013 | Snider |
| 8,530,173 B2 | 9/2013 | Lee |
| 8,597,958 B2 | 12/2013 | Lee |
| 8,617,825 B2 | 12/2013 | Snider et al. |
| 8,728,742 B2 | 5/2014 | Snider |
| 8,734,769 B2 | 5/2014 | Lee |
| 8,748,110 B2 | 6/2014 | Snider et al. |
| 8,748,116 B2 | 6/2014 | Lee |
| 8,871,452 B2 | 10/2014 | Lee |
| 9,057,733 B2 | 6/2015 | Snider et al. |
| 9,150,654 B2 | 10/2015 | Snider |
| 9,239,333 B2 | 1/2016 | Snider |
| D770,057 S | 10/2016 | Snider et al. |
| 9,523,696 B2 | 12/2016 | Snider |
| 9,551,708 B2 | 1/2017 | Snider et al. |
| 9,568,481 B2 | 2/2017 | Snider et al. |
| 2004/0048286 A1 | 3/2004 | Lee |
| 2007/0248981 A1 | 10/2007 | Snider et al. |
| 2009/0264779 A1 | 10/2009 | Snider et al. |

(Continued)

FOREIGN PATENT DOCUMENTS

| | | |
|---|---|---|
| CN | 106908604 | 6/2017 |
| EP | 2 734 222 | 10/2016 |

(Continued)

OTHER PUBLICATIONS

U.S. Appl. No. 14/244,526, filed Apr. 3, 2014, Snider et al.
U.S. Appl. No. 14/290,465, filed May 29, 2014, Lee.
U.S. Appl. No. 29/503,097, filed Sep. 23, 2014, Snider et al.
U.S. Appl. No. 29/503,095, filed Sep. 23, 2014, Snider et al.

(Continued)

*Primary Examiner* — Zachary C Howard
(74) *Attorney, Agent, or Firm* — Fish & Richardson P.C.

(57) ABSTRACT

Methods of treating a subject having a cardiovascular disease, selecting a therapy for a subject having a cardiovascular disease, identifying a subject having a cardiovascular disease that will benefit or not benefit from exercise therapy, determining whether a subject having a cardiovascular disease should begin, continue, not begin, discontinue, or avoid exercise therapy, determining whether a subject having a cardiovascular disease should continue, discontinue, or avoid exercise therapy, reducing the risk of an adverse outcome (e.g., death) in a subject having a cardiovascular disease, and predicting the efficacy of exercise therapy in a subject having a cardiovascular disease. These methods include determining a level of soluble ST2 in a subject.

8 Claims, 8 Drawing Sheets

Specification includes a Sequence Listing.

(56) References Cited

U.S. PATENT DOCUMENTS

| | | |
|---|---|---|
| 2009/0305265 A1 | 12/2009 | Snider et al. |
| 2010/0009356 A1 | 1/2010 | Snider et al. |
| 2010/0055683 A1 | 3/2010 | Snider et al. |
| 2011/0053170 A1 | 3/2011 | Snider et al. |
| 2011/0223106 A1 | 9/2011 | Rosjo et al. |
| 2011/0250703 A1 | 10/2011 | Lee |
| 2011/0262941 A1 | 10/2011 | Snider |
| 2011/0280887 A1 | 11/2011 | Lee |
| 2012/0040381 A1 | 2/2012 | Snider |
| 2012/0065897 A1 | 3/2012 | Snider |
| 2012/0276551 A1 | 11/2012 | Snider |
| 2013/0177931 A1 | 7/2013 | Snider |
| 2013/0244236 A1 | 9/2013 | Snider et al. |
| 2013/0251664 A1 | 9/2013 | Lee |
| 2013/0273562 A1 | 10/2013 | Lee |
| 2013/0317030 A1 | 11/2013 | Lee |
| 2013/0345805 A1 | 12/2013 | Snider et al. |
| 2014/0045200 A1 | 2/2014 | Snider |
| 2014/0051773 A1 | 2/2014 | Snider |
| 2014/0058743 A1 | 2/2014 | Snider et al. |
| 2014/0302536 A1 | 10/2014 | Snider et al. |
| 2015/0081224 A1 | 3/2015 | Snider et al. |
| 2015/0153360 A1 | 6/2015 | Lee |
| 2015/0177259 A1 | 6/2015 | Lee |
| 2015/0199491 A1 | 7/2015 | Snider et al. |
| 2015/0361177 A1 | 12/2015 | Snider |
| 2016/0169879 A1 | 6/2016 | Snider et al. |
| 2016/0169882 A1 | 6/2016 | Snider et al. |
| 2016/0299153 A1 | 10/2016 | Snider |

FOREIGN PATENT DOCUMENTS

| | | |
|---|---|---|
| GB | 2372114 | 8/2002 |
| JP | 2005-538700 | 12/2005 |
| JP | 2009-534691 | 9/2009 |
| JP | 6134316 | 5/2017 |
| JP | 6416974 | 10/2018 |
| RU | 2355295 | 5/2009 |
| WO | WO 03/94856 | 11/2003 |
| WO | WO 07/127749 | 11/2007 |
| WO | WO 07/130962 | 11/2007 |
| WO | WO 10/054810 | 5/2010 |
| WO | WO 2013/012945 | 1/2013 |
| WO | WO 2013/103390 | 7/2013 |

OTHER PUBLICATIONS

U.S. Appl. No. 15/370,049, filed Dec. 6, 2016, Snider et al.
U.S. Appl. No. 15/382,810, filed Dec. 19, 2016, Snider.
U.S. Appl. No. 15/385,095, filed Dec. 20, 2016, Snider et al.
U.S. Appl. No. 15/410,155, filed Jan. 19, 2017, Snider et al.
Aaronson, et al., "Development and prospective validation of a clinical index to predict survival in ambulatory patients referred for cardiac transplant evaluation," Circulation 95(12):2660-2667 (1997).
Ahmad et al., "Heart Failure Interaction Between ST2 Levels and Exercise Training in Patients With Chronic Heart Failure: Analysis from the HF-Action Trial," ACC Moderated Poster Contributions Session Title: Delineating Exercise-related and Hemodynamic Abnormalities in Chronic Heart Failure, JACC, Mar. 2012, 59: 1 page.
Bayes-Genis et al., "Soluble ST2 Monitoring Provides Additional Risk Stratification for Outpatients with Decompensated Heart Failure," Rev. Esp. Cardiol. 63(10):1171-1178, 2010.
Bilinska et al., "Influence of dynamic training on hemodynamic, neurohormonal responses to static exercise and on inflammatory markers in patients after coronary artery bypass grafting," Circulation Journal, Nov. 2010, 74: 2598-2604.
Bittner et al., "Prediction of mortality and morbidity with a 6-minute walk test in patients with left ventricular dysfunction. SOLVD Investigators," JAMA 270(14):1702-1707 (1993).
Boisot et al., "Serial sampling of ST2 predicts 90-day mortality following destabilized heart failure," J. Card. Fail. 14(9):732-738, 2008. Abstract only.
Daniels et al., "Association of ST2 Levels with Cardiac Structure and Function and Mortality in Outpatients," Am. Heart J. 160(4):721-728, 2010. Abstract only.
Examination Report No. 1 for Australian Patent Application No. 2012284039 dated May 23, 2016, 8 pages.
Extended European Search Report and Search Opinion for European Patent Appl. No. 12814331.0, dated Mar. 17, 2015, 6 pages.
Extended European Search Report in European Application No. 16192678.7, dated Feb. 24, 2017, 8 pages.
Final Office Action in U.S. Appl. No. 14/299,851, dated May 3, 2016, 7 pages.
First Mexican Office Action in Mexican Application No. MX/a/2014/000715, dated Oct. 12, 2016, 6 pages (with English translation).
First Office Action for Chinese Patent Application No. 201280045405.6, dated Nov. 3, 2014, 4 pages (with English translation).
International Preliminary Report on Patentability for PCT/US2012/047238, dated Jan. 21, 2014.
International Search Report issued in international application PCT/US2012/047238, dated Nov. 1, 2012.
Ivey et al., "Cardiovascular health and fitness after stroke," Topics in Stroke Rehabilitation, Jan. 2005, 12: pp. 1-16.
Korhonen et al., "Smoking cessation program with exercise improves cardiovascular disease biomarkers in sedentary women," Journal of Women's Health 20:1051-1064 (2011).
Ky et al., "High-sensitivity ST2 for prediction of adverse outcomes in chronic heart failure," Cir. Heart Fail. 4:180-187 (2011).
Lu et al., "Establishment of reference intervals for soluble ST2 from a United States population," Clin. Chim. Acta 411:21-22 (2010) (Abstract only).
Mancini et al., "Value of peak exercise oxygen consumption for optimal timing of cardiac transplantation in ambulatory patients with heart failure," Circulation 83:778-786 (1991).
Non-final Office Action in U.S. Appl. No. 13/552,533, dated Aug. 8, 2013, 11pages.
Non-final Office Action in U.S. Appl. No. 14/299,851, dated Aug. 6, 2015, 18 pages.
Notice for Reasons of Rejection issued for Japanese Patent Appl. No. 2014-521739 dated May 12, 2016, 10 pages (with English translation).
O'Connor et al., "Efficacy and safety of exercise training in patients with chronic heart failure, HF-ACTION randomized Controlled Trial," JAMA 301:1439-1450 (2009).
Office Action in Australian Application No. 2017204261, dated Mar. 9, 2018, 6 pages.
Office Action in Canadian Application No. 2,842,072, dated Apr. 24, 2018, 6 pages.
Office Action in Chinese Application No. 201610902184.X, dated Feb. 23, 2018, 4 pages (English translation).
Office Action in European Application No. 16192678.7, dated Jan. 5, 2018, 4 pages.
Office Action in Indian Application No. 419/DELNP/2014, dated Oct. 26, 2018, 6 pages (with English translation).
Office Action in Japanese Application No. 2017-084084, dated Feb. 26, 2018, 6 pages (with English translation).
Sanada et al., "ST2 is an Emerging Functional Biomarker Predicting Mortality after Acute Heart Events and Comprising Stress-Induced Cardioprotective Signaling System with IL-33," Circ. J. 73(Suppl. 1):25; Abstract #3, 2009.
Second Mexican Office Action in Mexican Application No. MX/a/2014/000715, dated Mar. 22, 2017, 8 pages (with English translation).
Second Office Action for Chinese Patent Application No. 201280045405.6, dated Jul. 16, 2015, 3 pages.
Third Office Action for Chinese Patent Application No. 210280045405.6, dated Dec. 22, 2015, 2 pages.
Troughton et al., "Outpatient Monitoring and Treatment of Chronic Heart Failure Guided by Amino-Terminal Pro-B-Type Natriuretic Peptide Measurement," American Journal of Cardiology, Feb. 2008, 101: S72-S75.
Written Opinion of the International Searching Authority issued in international application PCT/US2012/047238, dated Nov. 1, 2012.

(56) References Cited

OTHER PUBLICATIONS

BR Office Action in Brazilian Appln. No. BR112014001283-0, dated Apr. 15 2019, 6 pages (with English translation).
MX Office Action in Mexican Appln. No. MX/2017/013236, dated May 2, 2019, 8 pages (with English translation).
MX Office Action in Mexican Appln. No. MX/2017/013236, dated Nov. 11, 2019, 8 pages (with English translation).

```
Met Gly Phe Trp Ile Leu Ala Ile Leu Thr Ile Leu Met Tyr Ser Thr
1               5                   10                  15
Ala Ala Lys Phe Ser Lys Gln Ser Trp Gly Leu Glu Asn Glu Ala Leu
            20                  25                  30
Ile Val Arg Cys Pro Arg Gln Gly Lys Pro Ser Tyr Thr Val Asp Trp
            35                  40                  45
Tyr Tyr Ser Gln Thr Asn Lys Ser Ile Pro Thr Gln Glu Arg Asn Arg
        50                  55                  60
Val Phe Ala Ser Gly Gln Leu Leu Lys Phe Leu Pro Ala Ala Val Ala
65                  70                  75                  80
Asp Ser Gly Ile Tyr Thr Cys Ile Val Arg Ser Pro Thr Phe Asn Arg
                85                  90                  95
Thr Gly Tyr Ala Asn Val Thr Ile Tyr Lys Lys Gln Ser Asp Cys Asn
                100                 105                 110
Val Pro Asp Tyr Leu Met Tyr Ser Thr Val Ser Gly Ser Glu Lys Asn
            115                 120                 125
Ser Lys Ile Tyr Cys Pro Thr Ile Asp Leu Tyr Asn Trp Thr Ala Pro
        130                 135                 140
Leu Glu Trp Phe Lys Asn Cys Gln Ala Leu Gln Gly Ser Arg Tyr Arg
145                 150                 155                 160
Ala His Lys Ser Phe Leu Val Ile Asp Asn Val Met Thr Glu Asp Ala
                165                 170                 175
Gly Asp Tyr Thr Cys Lys Phe Ile His Asn Glu Asn Gly Ala Asn Tyr
                180                 185                 190
Ser Val Thr Ala Thr Arg Ser Phe Thr Val Lys Asp Glu Gln Gly Phe
            195                 200                 205
Ser Leu Phe Pro Val Ile Gly Ala Pro Ala Gln Asn Glu Ile Lys Glu
        210                 215                 220
Val Glu Ile Gly Lys Asn Ala Asn Leu Thr Cys Ser Ala Cys Phe Gly
225                 230                 235                 240
Lys Gly Thr Gln Phe Leu Ala Ala Val Leu Trp Gln Leu Asn Gly Thr
                245                 250                 255
Lys Ile Thr Asp Phe Gly Glu Pro Arg Ile Gln Gln Glu Glu Gly Gln
            260                 265                 270
Asn Gln Ser Phe Ser Asn Gly Leu Ala Cys Leu Asp Met Val Leu Arg
        275                 280                 285
Ile Ala Asp Val Lys Glu Glu Asp Leu Leu Leu Gln Tyr Asp Cys Leu
    290                 295                 300
Ala Leu Asn Leu His Gly Leu Arg Arg His Thr Val Arg Leu Ser Arg
305                 310                 315                 320
Lys Asn Pro Ser Lys Glu Cys Phe            (SEQ ID NO:1)
                325
```

Fig. 5

```
gaggagggac ctacaaagac tggaaactat tcttagctcc gtcactgact ccaagttcat   60
cccctctgtc tttcagtttg gttgagatat aggctactct tcccaactca gtcttgaaga  120
gtatcaccaa ctgcctcatg tgtggtgacc ttcactgtcg tatgccagtg actcatctgg  180
agtaatctca acaacgagtt accaatactt gctcttgatt gataaacaga atgggttttt  240
ggatcttagc aattctcaca attctcatgt attccacagc agcaaagttt agtaaacaat  300
catggggcct ggaaaatgag gctttaattg taagatgtcc tagacaagga aaacctagtt  360
acaccgtgga ttggtattac tcacaaacaa acaaaagtat tcccactcag gaaagaaatc  420
gtgtgtttgc ctcaggccaa cttctgaagt ttctaccagc tgcagttgct gattctggta  480
tttatacctg tattgtcaga agtcccacat tcaataggac tggatatgcg aatgtcacca  540
tatataaaaa acaatcagat tgcaatgttc cagattattt gatgtattca acagtatctg  600
gatcagaaaa aaattccaaa atttattgtc ctaccattga cctctacaac tggacagcac  660
ctcttgagtg gtttaagaat tgtcaggctc ttcaaggatc aaggtacagg gcgcacaagt  720
cattttggt cattgataat gtgatgactg aggacgcagg tgattacacc tgtaaattta  780
tacacaatga aaatggagcc aattatagtg tgacggcgac caggtccttc acggtcaagg  840
atgagcaagg cttttctctg tttccagtaa tcggagcccc tgcacaaaat gaaataaagg  900
aagtggaaat tggaaaaaac gcaaacctaa cttgctctgc ttgttttgga aaaggcactc  960
agttcttggc tgccgtcctg tggcagctta atggaacaaa aattacagac tttggtgaac 1020
caagaattca acaagaggaa gggcaaaatc aaagtttcag caatgggctg gcttgtctag 1080
acatggtttt aagaatagct gacgtgaagg aagaggattt attgctgcag tacgactgtc 1140
tggccctgaa tttgcatggc ttgagaaggc acaccgtaag actaagtagg aaaaatccaa 1200
gtaaggagtg tttctgagac tttgatcacc tgaactttct ctagcaagtg taagcagaat 1260
ggagtgtggt tccaagagat ccatcaagac aatgggaatg cctgtgcca taaaatgtgc 1320
ttctcttctt cgggatgttg tttgctgtct gatctttgta gactgttcct gtttgctggg 1380
agcttctctg ctgcttaaat tgttcgtcct cccccactcc ctcctatcgt tggtttgtct 1440
agaacactca gctgcttctt tggtcatcct tgttttctaa ctttatgaac tccctctgtg 1500
tcactgtatg tgaaaggaaa tgcaccaaca accgtaaact gaacgtgttc ttttgtgctc 1560
ttttataact tgcattacat gttgtaagca tggtccgttc tatacctttt tctggtcata 1620
atgaacactc attttgttag cgagggtgt aaagtgaaca aaaggggaa gtatcaaact 1680
actgccattt cagtgagaaa atcctaggtg ctactttata ataagacatt tgttaggcca 1740
ttcttgcatt gatataaaga aatacctgag actgggtgat ttatatgaaa agaggtttaa 1800
ttggctcaca gttctgcagg ctgtatggga agcatggcgg catctgcttc tggggacacc 1860
tcaggagctt tactcatggc agaaggcaaa gcaaaggcag gcacttcaca cagtaaaagc 1920
aggagcgaga gagaggtgcc acactgaaac agccagatct catgagaagt cactcactat 1980
tgcaaggaca gcatcaaaga gatggtgcta aaccattcat gatgaactca cccccatgat 2040
ccaatcacct cccaccaggc tccacctcga atactgggga ttaccattca gcatgagatt 2100
tgggcaggaa cacagaccca aaccatacca cacacattat cattgttaaa ctttgtaaag 2160
tatttaaggt acatggaaca cacgggaagt ctggtagctc agcccatttc tttattgcat 2220
ctgttattca ccatgtaatt caggtaccac gtattccagg gagcctttct tggccctcag 2280
tttgcagtat acacactttc caagtactct tgtagcatcc tgtttgtatc atagcactgg 2340
tcacattgcc ttacctaaat ctgtttgaca gtctgctcaa cacgactgca agctccatga 2400
gggcagggac atcatctctt ccatctttgg gtccttagtg caatacctgg cagctagcca 2460
gtgctcagct aaatatttgt tgactgaata aatgaatgca caaccaaaaa aaaaaaaaaa 2520
aaaaaaaaaa aaaaaaaaaa aa                                          2542
(SEQ ID NO:2)
```

Fig. 6

```
Met Gly Phe Trp Ile Leu Ala Ile Leu Thr Ile Leu Met Tyr Ser Thr
 1               5                  10                  15
Ala Ala Lys Phe Ser Lys Gln Ser Trp Gly Leu Glu Asn Glu Ala Leu
            20                  25                  30
Ile Val Arg Cys Pro Arg Gln Gly Lys Pro Ser Tyr Thr Val Asp Trp
            35                  40                  45
Tyr Tyr Ser Gln Thr Asn Lys Ser Ile Pro Thr Gln Glu Arg Asn Arg
        50                  55                  60
Val Phe Ala Ser Gly Gln Leu Leu Lys Phe Leu Pro Ala Ala Val Ala
 65                 70                  75                  80
Asp Ser Gly Ile Tyr Thr Cys Ile Val Arg Ser Pro Thr Phe Asn Arg
                85                  90                  95
Thr Gly Tyr Ala Asn Val Thr Ile Tyr Lys Lys Gln Ser Asp Cys Asn
            100                 105                 110
Val Pro Asp Tyr Leu Met Tyr Ser Thr Val Ser Gly Ser Glu Lys Asn
            115                 120                 125
Ser Lys Ile Tyr Cys Pro Thr Ile Asp Leu Tyr Asn Trp Thr Ala Pro
        130                 135                 140
Leu Glu Trp Phe Lys Asn Cys Gln Ala Leu Gln Gly Ser Arg Tyr Arg
145                 150                 155                 160
Ala His Lys Ser Phe Leu Val Ile Asp Asn Val Met Thr Glu Asp Ala
                165                 170                 175
Gly Asp Tyr Thr Cys Lys Phe Ile His Asn Glu Asn Gly Ala Asn Tyr
            180                 185                 190
Ser Val Thr Ala Thr Arg Ser Phe Thr Val Lys Asp Glu Gln Gly Phe
            195                 200                 205
Ser Leu Phe Pro Val Ile Gly Ala Pro Ala Gln Asn Glu Ile Lys Glu
        210                 215                 220
Val Glu Ile Gly Lys Asn Ala Asn Leu Thr Cys Ser Ala Cys Phe Gly
225                 230                 235                 240
Lys Gly Thr Gln Phe Leu Ala Ala Val Leu Trp Gln Leu Asn Gly Thr
                245                 250                 255
Lys Ile Thr Asp Phe Gly Glu Pro Arg Ile Gln Gln Glu Glu Gly Gln
            260                 265                 270
Asn Gln Ser Phe Ser Asn Gly Leu Ala Cys Leu Asp Met Val Leu Arg
        275                 280                 285
Ile Ala Asp Val Lys Glu Glu Asp Leu Leu Leu Gln Tyr Asp Cys Leu
        290                 295                 300
Ala Leu Asn Leu His Gly Leu Arg Arg His Thr Val Arg Leu Ser Arg
305                 310                 315                 320
Lys Asn Pro Ile Asp His His Ser Ile Tyr Cys Ile Ile Ala Val Cys
            325                 330                 335
Ser Val Phe Leu Met Leu Ile Asn Val Leu Val Ile Ile Leu Lys Met
            340                 345                 350
Phe Trp Ile Glu Ala Thr Leu Leu Trp Arg Asp Ile Ala Lys Pro Tyr
        355                 360                 365
Lys Thr Arg Asn Asp Gly Lys Leu Tyr Asp Ala Tyr Val Val Tyr Pro
370                 375                 380
Arg Asn Tyr Lys Ser Ser Thr Asp Gly Ala Ser Arg Val Glu His Phe
385                 390                 395                 400
```

Fig. 7A

```
Val His Gln Ile Leu Pro Asp Val Leu Glu Asn Lys Cys Gly Tyr Thr
            405                     410                 415
Leu Cys Ile Tyr Gly Arg Asp Met Leu Pro Gly Glu Asp Val Val Thr
            420                     425                 430
Ala Val Glu Thr Asn Ile Arg Lys Ser Arg Arg His Ile Phe Ile Leu
            435                     440                 445
Thr Pro Gln Ile Thr His Asn Lys Glu Phe Ala Tyr Glu Gln Glu Val
        450                 455                 460
Ala Leu His Cys Ala Leu Ile Gln Asn Asp Ala Lys Val Ile Leu Ile
465                     470                 475                 480
Glu Met Glu Ala Leu Ser Glu Leu Asp Met Leu Gln Ala Glu Ala Leu
                    485                 490                 495
Gln Asp Ser Leu Gln His Leu Met Lys Val Gln Gly Thr Ile Lys Trp
            500                     505                 510
Arg Glu Asp His Ile Ala Asn Lys Arg Ser Leu Asn Ser Lys Phe Trp
            515                     520                 525
Lys His Val Arg Tyr Gln Met Pro Val Pro Ser Lys Ile Pro Arg Lys
    530                     535                 540
Ala Ser Ser Leu Thr Pro Leu Ala Ala Gln Lys Gln    (SEQ ID NO:3)
545                 550                 555
```

Fig. 7B

```
aaagagaggc tggctgttgt atttagtaaa gctataaagc tgtaagagaa attggctttc  60
tgagttgtga aactgtgggc agaaagttga ggaagaaaga actcaagtac aacccaatga 120
ggttgagata taggctactc ttcccaactc agtcttgaag agtatcacca actgcctcat 180
gtgtggtgac cttcactgtc gtatgccagt gactcatctg gagtaatctc aacaacgagt 240
taccaatact tgctcttgat tgataaacag aatggggttt tggatcttag caattctcac 300
aattctcatg tattccacag cagcaaagtt tagtaaacaa tcatggggcc tggaaaatga 360
ggctttaatt gtaagatgtc ctagacaagg aaaacctagt tacaccgtgg attggtatta 420
ctcacaaaca aacaaagta ttcccactca ggaaagaaat cgtgtgtttg cctcaggcca 480
acttctgaag tttctaccag ctgcagttgc tgattctggt atttatacct gtattgtcag 540
aagtcccaca ttcaatagga ctggatatgc gaatgtcacc atatataaaa aacaatcaga 600
ttgcaatgtt ccagattatt tgatgtattc aacagtatct ggatcagaaa aaaattccaa 660
aatttattgt cctaccattg acctctacaa ctggacagca cctcttgagt ggtttaagaa 720
ttgtcaggct cttcaaggat caaggtacag ggcgcacaag tcattttgg tcattgataa 780
tgtgatgact gaggacgcag gtgattacac ctgtaaattt atacacaatg aaaatggagc 840
caattatagt gtgacggcga ccaggtcctt cacggtcaag gatgagcaag ctttctctct 900
gtttccagta atcggagccc ctgcacaaaa tgaaataaag gaagtggaaa ttggaaaaaa 960
cgcaaaccta acttgctctg cttgttttgg aaaaggcact cagttcttgg ctgccgtcct 1020
gtggcagctt aatggaacaa aaattacaga ctttggtgaa ccaagaattc aacaagagga 1080
agggcaaaat caaagtttca gcaatgggct ggcttgtcta gacatggttt taagaatagc 1140
tgacgtgaag gaagaggatt tattgctgca gtacgactgt ctggccctga atttgcatgg 1200
cttgagaagg cacaccgtaa gactaagtag gaaaaatcca attgatcatc atagcatcta 1260
ctgcataatt gcagtatgta gtgtatttt aatgctaatc aatgtcctgg ttatcatcct 1320
aaaaatgttc tggattgagg ccactctgct ctggagagac atagctaaac cttacaagac 1380
taggaatgat ggaaagctct atgatgctta tgttgtctac ccacgaaact acaaatccag 1440
tacagatggg gccagtcgtg tagagcactt tgttcaccag attctgcctg atgttcttga 1500
aaataaatgt ggctatacct tatgcattta tgggagagat atgctacctg gagaagatgt 1560
agtcactgca gtggaaacca acatacgaaa gagcaggcgg cacattttca tcctgacccc 1620
tcagatcact cacaataagg agtttgccta cgagcaggag gttgccctgc actgtgccct 1680
catccagaac gacgccaagg tgatacttat tgagatggag gctctgagcg agctggacat 1740
gctgcaggct gaggcgcttc aggactccct ccagcatctt atgaaagtac agggaccat 1800
caagtggagg gaggaccaca ttgccaataa aagtccctg aattctaaat tctggaagca 1860
cgtgaggtac caaatgcctg tgccaagcaa aattcccaga aaggcctcta gtttgactcc 1920
cttggctgcc cagaagcaat agtgcctgct gtgatgtgca aaggcatctg agtttgaagc 1980
tttcctgact tctcctagct ggcttatgcc cctgcactga agtgtgagga gcaggaatat 2040
taaagggatt caggcctc                                              2058
(SEQ ID NO:4)
```

Fig. 8

SEQUENCE LISTING

<160> NUMBER OF SEQ ID NOS: 4

<210> SEQ ID NO 1
<211> LENGTH: 328
<212> TYPE: PRT
<213> ORGANISM: Homo sapiens

<400> SEQUENCE: 1

```
Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
```

```
              275                 280                 285
Ile Ala Asp Val Lys Glu Glu Asp Leu Leu Leu Gln Tyr Asp Cys Leu
        290                 295                 300

Ala Leu Asn Leu His Gly Leu Arg Arg His Thr Val Arg Leu Ser Arg
305                 310                 315                 320

Lys Asn Pro Ser Lys Glu Cys Phe
                325

<210> SEQ ID NO 2
<211> LENGTH: 2542
<212> TYPE: DNA
<213> ORGANISM: Homo sapiens

<400> SEQUENCE: 2
```

| | | | | |
|---|---|---|---|---|
| gaggagggac | ctacaaagac | tggaaactat | tcttagctcc | gtcactgact | ccaagttcat | 60 |
| cccctctgtc | tttcagtttg | gttgagatat | aggctactct | tcccaactca | gtcttgaaga | 120 |
| gtatcaccaa | ctgcctcatg | tgtggtgacc | ttcactgtcg | tatgccagtg | actcatctgg | 180 |
| agtaatctca | caacgagtt | accaatactt | gctcttgatt | gataaacaga | atggggtttt | 240 |
| ggatcttagc | aattctcaca | attctcatgt | attccacagc | agcaaagttt | agtaaacaat | 300 |
| catggggcct | ggaaaatgag | gctttaattg | taagatgtcc | tagacaagga | aaacctagtt | 360 |
| acaccgtgga | ttggtattac | tcacaaacaa | acaaaagtat | tcccactcag | gaaagaaatc | 420 |
| gtgtgtttgc | ctcaggccaa | cttctgaagt | ttctaccagc | tgcagttgct | gattctggta | 480 |
| tttatacctg | tattgtcaga | agtcccacat | tcaataggac | tggatatgcg | aatgtcacca | 540 |
| tatataaaaa | acaatcagat | tgcaatgttc | cagattattt | gatgtattca | acagtatctg | 600 |
| gatcagaaaa | aaattccaaa | atttattgtc | ctaccattga | cctctacaac | tggacagcac | 660 |
| ctcttgagtg | gtttaagaat | tgtcaggctc | ttcaaggatc | aaggtacagg | gcgcacaagt | 720 |
| catttttggt | cattgataat | gtgatgactg | aggacgcagg | tgattacacc | tgtaaattta | 780 |
| tacacaatga | aaatggagcc | aattatagtg | tgacggcgac | caggtccttc | acggtcaagg | 840 |
| atgagcaagg | cttttctctg | tttccagtaa | tcggagcccc | tgcacaaaat | gaaataaagg | 900 |
| aagtggaaat | tggaaaaaac | gcaaacctaa | cttgctctgc | ttgttttgga | aaaggcactc | 960 |
| agttcttggc | tgccgtcctg | tggcagctta | atggaacaaa | aattacagac | tttggtgaac | 1020 |
| caagaattca | acaagaggaa | gggcaaaatc | aaagtttcag | caatgggctg | gcttgtctag | 1080 |
| acatggtttt | aagaatagct | gacgtgaagg | aagaggattt | attgctgcag | tacgactgtc | 1140 |
| tggccctgaa | tttgcatggc | ttgagaaggc | acaccgtaag | actaagtagg | aaaaatccaa | 1200 |
| gtaaggagtg | tttctgagac | tttgatcacc | tgaactttct | ctagcaagtg | taagcagaat | 1260 |
| ggagtgtggt | tccaagagat | ccatcaagac | aatgggaatg | gcctgtgcca | taaaatgtgc | 1320 |
| ttctcttctt | cgggatgttg | tttgctgtct | gatctttgta | gactgttcct | gtttgctggg | 1380 |
| agcttctctg | ctgcttaaat | tgttcgtcct | cccccactcc | ctcctatcgt | tggtttgtct | 1440 |
| agaacactca | gctgcttctt | tggtcatcct | tgttttctaa | ctttatgaac | tccctctgtg | 1500 |
| tcactgtatg | tgaaaggaaa | tgcaccaaca | accgtaaact | gaacgtgttc | ttttgtgctc | 1560 |
| ttttataact | tgcattacat | gttgtaagca | tggtccgttc | tataccttt | tctggtcata | 1620 |
| atgaacactc | attttgttag | cgagggtggt | aaagtgaaca | aaaaggggaa | gtatcaaact | 1680 |
| actgccattt | cagtgagaaa | atcctaggtg | ctactttata | ataagacatt | tgttaggcca | 1740 |
| ttcttgcatt | gatataaaga | aatacctgag | actgggtgat | ttatatgaaa | agaggtttaa | 1800 |

-continued

```
ttggctcaca gttctgcagg ctgtatggga agcatggcgg catctgcttc tggggacacc   1860
tcaggagctt tactcatggc agaaggcaaa gcaaaggcag gcacttcaca cagtaaaagc   1920
aggagcgaga gagaggtgcc acactgaaac agccagatct catgagaagt cactcactat   1980
tgcaaggaca gcatcaaaga gatggtgcta aaccattcat gatgaactca cccccatgat   2040
ccaatcacct cccaccaggc tccacctcga atactgggga ttaccattca gcatgagatt   2100
tgggcaggaa cacagaccca aaccatacca cacacattat cattgttaaa ctttgtaaag   2160
tatttaaggt acatggaaca cacgggaagt ctggtagctc agcccatttc tttattgcat   2220
ctgttattca ccatgtaatt caggtaccac gtattccagg gagcctttct tggccctcag   2280
tttgcagtat acacactttc caagtactct tgtagcatcc tgtttgtatc atagcactgg   2340
tcacattgcc ttacctaaat ctgtttgaca gtctgctcaa cacgactgca agctccatga   2400
gggcagggac atcatctctt ccatctttgg gtccttagtg caatacctgg cagctagcca   2460
gtgctcagct aaatatttgt tgactgaata aatgaatgca caaccaaaaa aaaaaaaaa    2520 aaaaaaaaa aaaaaaaaa aa                                              2542
```

<210> SEQ ID NO 3
<211> LENGTH: 556
<212> TYPE: PRT
<213> ORGANISM: Homo sapiens

<400> SEQUENCE: 3

```
Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
                20                  25                  30

Ile Val Arg Cys Pro Arg Gln Gly Lys Pro Ser Tyr Thr Val Asp Trp
            35                  40                  45

Tyr Tyr Ser Gln Thr Asn Lys Ser Ile Pro Thr Gln Glu Arg Asn Arg
        50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240
```

Lys Gly Thr Gln Phe Leu Ala Ala Val Leu Trp Gln Leu Asn Gly Thr
            245                 250                 255

Lys Ile Thr Asp Phe Gly Glu Pro Arg Ile Gln Gln Glu Glu Gly Gln
        260                 265                 270

Asn Gln Ser Phe Ser Asn Gly Leu Ala Cys Leu Asp Met Val Leu Arg
    275                 280                 285

Ile Ala Asp Val Lys Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
                325                 330                 335

Ser Val Phe Leu Met Leu Ile Asn Val Leu Val Ile Ile Leu Lys Met
            340                 345                 350

Phe Trp Ile Glu Ala Thr Leu Leu Trp Arg Asp Ile Ala Lys Pro Tyr
        355                 360                 365

Lys Thr Arg Asn Asp Gly Lys Leu Tyr Asp Ala Tyr Val Val Tyr Pro
    370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
                405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
        435                 440                 445

Thr Pro Gln Ile Thr His Asn Lys Glu Phe Ala Tyr Glu Gln Glu Val
    450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Gln His Leu Met Lys Val Gln Gly Thr Ile Lys Trp
            500                 505                 510

Arg Glu Asp His Ile Ala Asn Lys Arg Ser Leu Asn Ser Lys Phe Trp
        515                 520                 525

Lys His Val Arg Tyr Gln Met Pro Val Pro Ser Lys Ile Pro Arg Lys
    530                 535                 540

Ala Ser Ser Leu Thr Pro Leu Ala Ala Gln Lys Gln
545                 550                 555

<210> SEQ ID NO 4
<211> LENGTH: 2058
<212> TYPE: DNA
<213> ORGANISM: Homo sapiens

<400> SEQUENCE: 4
aaagagaggc tggctgttgt atttagtaaa gctataaagc tgtaagagaa attggctttc      60
tgagttgtga aactgtgggc agaaagttga ggaagaaaga actcaagtac aacccaatga    120
ggttgagata taggctactc ttcccaactc agtcttgaag agtatcacca actgcctcat    180
gtgtggtgac cttcactgtc gtatgccagt gactcatctg gagtaatctc aacaacgagt    240
taccaatact tgctcttgat tgataaacag aatgggtttt ggatcttag caattctcac     300 aattctcatg tattccacag cagcaaagtt tagtaaacaa tcatgggcc tggaaaatga     360

-continued

```
ggctttaatt gtaagatgtc ctagacaagg aaaacctagt tacaccgtgg attggtatta      420
ctcacaaaca aacaaaagta ttcccactca ggaaagaaat cgtgtgtttg cctcaggcca      480
acttctgaag tttctaccag ctgcagttgc tgattctggt atttatacct gtattgtcag      540
aagtcccaca ttcaatagga ctggatatgc gaatgtcacc atatataaaa aacaatcaga      600
ttgcaatgtt ccagattatt tgatgtattc aacagtatct ggatcagaaa aaaattccaa      660
aatttattgt cctaccattg acctctacaa ctggacagca cctcttgagt ggtttaagaa      720
ttgtcaggct cttcaaggat caaggtacag ggcgcacaag tcattttggg tcattgataa      780
tgtgatgact gaggacgcag gtgattacac ctgtaaattt atacacaatg aaaatggagc      840
caattatagt gtgacggcga ccaggtcctt cacggtcaag gatgagcaag gcttttctct      900
gtttccagta atcggagccc ctgcacaaaa tgaaataaag gaagtggaaa ttggaaaaaa      960
cgcaaaccta acttgctctg cttgttttgg aaaaggcact cagttcttgg ctgccgtcct     1020
gtggcagctt aatggaacaa aaattacaga ctttggtgaa ccaagaattc aacaagagga     1080
agggcaaaat caaagtttca gcaatgggct ggcttgtcta gacatggttt taagaatagc     1140
tgacgtgaag gaagaggatt tattgctgca gtacgactgt ctggccctga atttgcatgg     1200
cttgagaagg cacaccgtaa gactaagtag gaaaaatcca attgatcatc atagcatcta     1260
ctgcataatt gcagtatgta gtgtattttt aatgctaatc aatgtcctgg ttatcatcct     1320
aaaaatgttc tggattgagg ccactctgct ctggagagac atagctaaac cttacaagac     1380
taggaatgat ggaaagctct atgatgctta tgttgtctac ccacggaact acaaatccag     1440
tacagatggg gccagtcgtg tagagcactt tgttcaccag attctgcctg atgttcttga     1500
aaataaatgt ggctatacct tatgcattta tgggagagat atgctacctg gagaagatgt     1560
agtcactgca gtggaaacca acatacgaaa gagcaggcgg cacattttca tcctgacccc     1620
tcagatcact cacaataagg agtttgccta cgagcaggag gttgccctgc actgtgccct     1680
catccagaac gacgccaagg tgatacttat tgagatggag gctctgagcg agctggacat     1740
gctgcaggct gaggcgcttc aggactccct ccagcatctt atgaaagtac aggggaccat     1800
caagtggagg gaggaccaca ttgccaataa aaggtccctg aattctaaat tctggaagca     1860
cgtgaggtac caaatgcctg tgccaagcaa aattcccaga aaggcctcta gtttgactcc     1920
cttggctgcc cagaagcaat agtgcctgct gtgatgtgca aaggcatctg agtttgaagc     1980
tttcctgact tctcctagct ggcttatgcc cctgcactga agtgtgagga gcaggaatat     2040
taaagggatt caggcctc                                                   2058
```

METHODS OF TREATING CARDIOVASCULAR DISEASES AND PREDICTING THE EFFICACY OF EXERCISE THERAPY

CLAIM OF PRIORITY

This application is a continuation of U.S. patent application Ser. No. 15/409,283, filed on Jan. 18, 2017, which is a continuation of U.S. patent application Ser. No. 14/299,851, filed on Jun. 9, 2014, now issued as U.S. Pat. No. 9,551,708, which is a continuation of U.S. patent application Ser. No. 13/552,533, filed on Jul. 18, 2012, now issued as U.S. Pat. No. 8,748,110, which claims the benefit of U.S. Provisional Patent Application Ser. No. 61/508,923, filed on Jul. 18, 2011, and U.S. Provisional Patent Application Ser. No. 61/509,359, filed on Jul. 19, 2011, the entire contents of each of which are hereby incorporated by reference.

TECHNICAL FIELD

This invention relates to methods of treating cardiovascular diseases using exercise therapy, and predicting the efficacy of exercise therapy.

BACKGROUND

Circulating biomarkers play a critical role in the diagnosis and management of patients with chronic heart failure (Braunwald, *N. Engl. J. Med.* 358:2148-2159, 2008). Natriuretic peptides, such as brain natriuretic peptide (BNP) and N-terminal pro-BNP (NT-proBNP), have been demonstrated to be powerful tools for the diagnosis, risk stratification, and management of patients with heart failure (Felker et al., *Canadian Med. Assoc. J.* 175:611-617, 2006). In addition to being useful for clinical management, biomarkers can provide insights into the mechanisms underlying important physiologic relationships. Exercise intolerance, typically manifested as exertional dyspnea, is a major morbidity of chronic heart failure. Both maximal (e.g., as measured by peak oxygen uptake [peak VO$_2$]) (Aaronson et al., *Circulation* 95:2660-2667, 1997; Mancini et al., *Circulation* 83:778-786, 1991) and submaximal exercise capacity (e.g., as measured by distance in the 6-minute walk test) (Bittner et al., *JAMA* 270:1702-1707, 1993) have been demonstrated to be of substantial prognostic importance in chronic heart failure.

A variety of therapies can be used to treat patients diagnosed with a cardiovascular disease. For example, exercise therapy is commonly used to treat patients diagnosed with a cardiovascular disease (see, for example, Korhonen et al., *J. Womens Health* 20:1051-1064, 2011).

SUMMARY

Applicants have discovered a correlation between the level of soluble ST2 and the efficacy of exercise therapy in subjects having a cardiovascular disease, and a correlation between soluble ST2 level, exercise therapy, and the risk of an adverse outcome (e.g., death) in a subject having a cardiovascular disease.

Provided herein are methods of treating a subject having a cardiovascular disease that, in some embodiments, include determining a level of soluble ST2 in a biological sample from the subject, identifying a subject that has a decreased level of soluble ST2 in the biological sample compared to a risk reference level of soluble ST2, and selecting the identified subject for exercise therapy. Also provided are methods of treating a subject having a cardiovascular disease that include determining a level of soluble ST2 in a biological sample from the subject, identifying a subject that has an elevated level of soluble ST2 in the biological sample compared to a risk reference level of soluble ST2; and instructing the identified subject not to begin, to discontinue, or to avoid exercise therapy.

Also provided are methods of selecting a therapy for a subject having a cardiovascular disease that include determining a level of soluble ST2 in a biological sample from the subject, and comparing the level of soluble ST2 in the biological sample to a risk reference level of soluble ST2, where a decreased level of soluble ST2 in the biological sample compared to the risk reference level indicates that the subject should begin or continue exercise therapy, and an elevated level of soluble ST2 in the biological sample compared to the risk reference level indicates that the subject should not begin or should discontinue exercise therapy.

Also provided are methods of identifying a subject having a cardiovascular disease that will benefit from exercise therapy that include determining a level of soluble ST2 in a biological sample from the subject, and selecting a subject that has a decreased level of soluble ST2 in the biological sample as compared to a risk reference level of soluble ST2, where the selected subject is identified as a subject that will benefit from exercise therapy. Also provided are methods of identifying a subject having a cardiovascular disease that will not benefit from exercise therapy that include determining a level of soluble ST2 in a biological sample from the subject, and selecting a subject that has an elevated level of soluble ST2 in the biological sample compared to a risk reference level of soluble ST2, where the selected subject is identified as a subject that will not benefit from exercise therapy.

Also provided are methods of determining whether a subject having a cardiovascular disease should begin, continue, not begin, or discontinue exercise therapy that include determining a level of soluble ST2 in a biological sample from the subject, where a decreased level of soluble ST2 in the biological sample compared to a risk reference level of soluble ST2 indicates that the subject should begin or continue exercise therapy, and an elevated level of soluble ST2 indicates that the subject should not begin or discontinue exercise therapy.

Also provided are methods of determining whether a subject having a cardiovascular disease should discontinue or continue exercise therapy that include determining a level of soluble ST2 in a biological sample from the subject at a first time point before or after the start of exercise therapy, and determining a level of soluble ST2 in a biological sample from the subject undergoing exercise therapy at a second time point after the start of exercise therapy and after the first time point, where an elevation in the level of soluble ST2 in the biological sample at the second time point compared to the level of soluble ST2 in the biological sample at the first time point indicates that the subject should discontinue exercise therapy, and a decrease in the level of soluble ST2 in the biological sample at the second time point compared to the level of soluble ST2 in the biological sample at the first time point indicates that the subject should continue exercise therapy.

In some embodiments of the methods described herein, the methods include determining that the subject has a level of soluble ST2 that is above a first reference level (e.g., a first level indicating that the subject has a cardiovascular disease, or is at risk of an adverse cardiovascular event; e.g., as described in U.S. Pat. No. 7,998,683; US2011/0262941; US2012/0040381; 8,090,562; US2012/0065897; 7,670,769; 7,655,415; 7,989,210; US2011/0250703; 7,432,060; 7,985,558; US2011/028088, all of which are incorporated herein by reference) and below a second, risk reference level (e.g., below a level indicating that the subject is at risk of an adverse event if they engage in exercise, as described herein), and the subject is selected for exercise therapy. Thus in some embodiments, the methods include determining that the subject has a level of ST2 that falls within a range that is associated with the presence of a cardiovascular disease that would benefit from exercise therapy and the absence of high risk of an adverse event associated with exercise therapy.

Also provided are methods of reducing the risk of an adverse outcome in a subject having a cardiovascular disease that include determining a level of soluble ST2 in a biological sample from the subject, identifying a subject that has a decreased level of soluble ST2 in the biological sample compared to a risk reference level of soluble ST2, and selecting the identified subject for exercise therapy. Also provided are methods of reducing the risk of an adverse outcome in a subject having a cardiovascular disease that include determining a level of soluble ST2 in a biological sample from the subject, identifying a subject that has an elevated level of soluble ST2 in the biological sample compared to a risk reference level of soluble ST2, and instructing the subject to not begin or to discontinue exercise therapy. In some embodiments of these methods, the risk of adverse outcome is risk of death.

Also provided are methods of predicting the efficacy of exercise therapy in a subject having a cardiovascular disease that include determining a level of soluble ST2 in a biological sample from the subject, and comparing the level of soluble ST2 in the biological sample to an efficacy reference level of soluble ST2, where a decreased level of soluble ST2 in the biological sample compared to the efficacy reference level of soluble ST2 indicates that the exercise therapy will be effective in the subject, and an elevated level of soluble ST2 in the biological sample compared to the efficacy reference level of soluble ST2 indicates that the exercise therapy will not be effective in the subject.

In any of the methods described herein, the biological sample contains blood or serum. In any of the methods described herein, the determining is performed using an antibody or an antibody fragment that binds to soluble ST2. In any of the methods described herein, the reference level of soluble ST2 is a predetermined threshold value. In any of the methods described herein, the reference level of soluble ST2 is a level of soluble ST2 in a healthy subject. In any of the methods described herein, the subject is hyperchlosterolemic, hypertriglyceridemic, hyperlipidemic, a smoker, hypertensive, or has a body mass index of greater than 30. Some embodiments of the methods described herein further include determining a level of cardiac troponin I, B-type natriuretic peptide, atrial natriuretic peptide, or C-reactive protein in the biological sample. Some embodiments of the methods described herein further include determining a level of level of cardiac troponin I, B-type natriuretic peptide, atrial natriuretic peptide, or C-reactive protein in the biological sample at the first time point or the biological sample at the second time point.

In some embodiments of any of the methods described herein, the cardiovascular disease is selected from the group of: cardiac hypertrophy, myocardial infarction, stroke, arteriosclerosis, and heart failure. In some embodiments of any of the methods described herein, the subject is administered at least one therapeutic agent selected from the group of: anti-inflammatory agents, anti-thrombotic agents, anti-coagulants, anti-platelet agents, lipid-reducing agents (e.g., a statin), direct thrombin inhibitors, glycoprotein IIb/IIIb receptor inhibitors, calcium channel blockers, beta-adrenergic receptor blockers, cyclooxygenase-2 inhibitors, and renin-angiotensin-aldosterone system (RAAS) inhibitors. In some embodiments, the RAAS inhibitor is selected from the group of: an angiotensin-converting enzyme inhibitor, an angiotensin II receptor blocker, and an aldosterone antagonist.

As used herein, the term "cardiovascular disease" refers to a disorder of the heart and blood vessels, and includes disorders of the arteries, veins, arterioles, venules, and capillaries. Non-limiting examples of cardiovascular diseases include cardiac hypertrophy, myocardial infarction, stroke, arteriosclerosis, and heart failure. Additional examples of cardiovascular diseases are known in the art.

By the term "soluble ST2" is meant a soluble protein containing a sequence at least 90% identical (e.g., at least 95%, 96%, 97%, 98%, 99%, or 100% identical) to NCBI Accession No. NP_003847.2 (SEQ ID NO: 1) or containing a sequence at least 90% identical (e.g., at least 95%, 96%, 97%, 98%, 99%, or 100% identical) to amino acids 19-328 of SEQ ID NO: 1, or a nucleic acid containing a sequence at least 90% identical (e.g., at least 95%, 96%, 97%, 98%, 99%, or 100% identical) to NCBI Accession No. NM_003856.2 (SEQ ID NO: 2) or containing a sequence at least 90% identical (e.g., at least 95%, 96%, 97%, 98%, 99%, or 100% identical) to nucleotides 285 to 1214 of SEQ ID NO: 2.

By the term "elevated" or "elevation" is meant a difference, e.g., the presence of a statistically significant or detectable increase in a determined or measured level (e.g., a human soluble ST2 protein level) compared to a reference level (e.g., a level of human soluble ST2 in a subject not having a disease, a subject not presenting with two or more symptoms of a disease, or a subject not identified as being at risk of developing a disease, or a threshold level of human soluble ST2). In some embodiments, the reference is a threshold level, and any level above that is considered "elevated." Additional reference levels of human soluble ST2 are described herein and are known in the art.

By the term "reference level" is meant a threshold level or a level in a control subject or control patient population. A reference level will depend on the assay performed and can be determined by one of ordinary skill in the art. Non-limiting examples of reference levels are described herein and are known in the art. Reference levels of human soluble ST2 can be determined using methods known in the art.

In some embodiments, the reference level is a risk reference level, e.g., a risk reference level of soluble ST2 in a subject who experienced or was more likely to experience an adverse outcome and engaged in exercise, a level in a population of subjects who experienced or were more likely to experience an adverse outcome and engaged in exercise, or a threshold level of soluble ST2 above which the risk of an adverse outcome is increased in those who engage in exercise therapy.

In some embodiments, the reference level is an efficacy reference level, e.g., an efficacy reference level of soluble ST2 is a level in a subject who experienced a therapeutic benefit from exercise therapy, a level in a population of subjects who experienced a therapeutic benefit from exercise therapy, or a threshold level of soluble ST2 below which the subject is likely to experience a therapeutic benefit from exercise therapy.

By the term "additional marker" is meant a protein, nucleic acid, lipid, or carbohydrate, or a combination (e.g., two or more) thereof, that is diagnostic of the presence of a particular disease. The methods described herein can include detecting the level of soluble human ST2 and at least one additional marker in a biological sample from a subject. Non-limiting examples of additional markers that can be detected include: proANP, NT-proANP, ANP, proBNP, NT-proBNP, BNP, troponin, CRP, creatinine, Blood Urea Nitrogen (BUN), liver function enzymes, albumin, and bacterial endotoxin; and those markers described in U.S. Patent Application Publication Nos.: 2007/0248981; 2011/0053170; 2010/0009356; 2010/0055683; and 2009/0264779 (each of which is hereby incorporated by reference).

By the term "hypertriglyceridemia" is meant a triglyceride level that is greater than or equal to 180 ng/mL (e.g., greater than or equal to 200 ng/mL).

By the term "hypercholesterolemia" is meant an increased level of at least one form of cholesterol or total cholesterol in a subject. For example, a subject with hypercholesterolemia can have a high density lipoprotein (HDL) level of ≥40 mg/dL (e.g., ≥50 mg/dL or ≥60 mg/mL), a low density lipoprotein (LDL) level of ≥130 mg/dL (e.g., ≥160 mg/dL or ≥200 mg/dL), and/or a total cholesterol level of ≥200 mg/dL (e.g., 240 mg/dL).

By the term "hypertension" is meant an increased level of systolic and/or diastolic blood pressure. For example, a subject with hypertension can have a systolic blood pressure that is ≥120 mmHg (e.g., ≥140 mmHg or ≥160 mmHg) and/or a diastolic blood pressure that is ≥80 mmHg (e.g., ≥90 mmHg or ≥100 mmHg).

By the term "healthy subject" is meant a subject that does not have a disease (e.g., cardiovascular disease). For example, a healthy subject has not been diagnosed as having a disease and is not presenting with two or more (e.g., two, three, four, or five) symptoms of a disease state.

By "risk of death" is meant the risk of death in a subject from a disease or complications associated with a disease (e.g., a cardiovascular disease) compared to a reference population. The term risk of death as used herein excludes intentional or accidental death, e.g., death by blunt or crushing trauma, such as a car accident.

As used herein, a "biological sample" includes one or more of blood, serum, plasma, urine, and body tissue. Generally, a biological sample is a sample containing serum, blood, or plasma.

By the term "statin" is meant a therapeutic molecule that inhibits the enzyme HMG-CoA reductase. Non-limiting examples of statins include: atorvastatin, fluvastatin, lovastatin, pitavastatin, pravastatin, rosuvastatin, and simvastatin. Additional examples of statins are known in the art.

By "adverse outcome" is meant any detrimental event that occurs in a subject as a result of a disease (e.g., a cardiovascular disease). Non-limiting examples of adverse outcomes in a subject having a cardiovascular disease include: organ failure, organ transplantation, hospitalization or rehospitalization, recurrence of one or more symptoms of a cardiovascular disease, development of one or more additional symptoms of a cardiovascular disease, an increase in the frequency, intensity, or duration of one or more symptoms of a cardiovascular disease experienced by the subject, a first or subsequent myocardial infarction, or death (mortality). In preferred embodiments, the adverse outcome is mortality.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5 shows the protein sequence of Soluble Human ST2. Signal Peptide Amino acids 1-18 (underlined); Mature Peptide after removal of signal sequence amino acids (19-328).

FIG. 6 shows the mRNA sequence of soluble human ST2. Nucleotides 285 to 1214 encode the amino acid sequence (without the signal sequence) of soluble human ST2.

FIGS. 7A-B shows the protein sequence of the long form of human St2 (membrane-bound). Signal Peptide Amino acids 1-18 (underlined); Mature Peptide after removal of signal sequence amino acids (19-556).

FIG. 8 shows the mRNA sequence of human ST2. Nucleotides 326 to 1939 encode the amino acid sequence (without the signal sequence) of the long form of human ST2.

DETAILED DESCRIPTION

Figure 1:
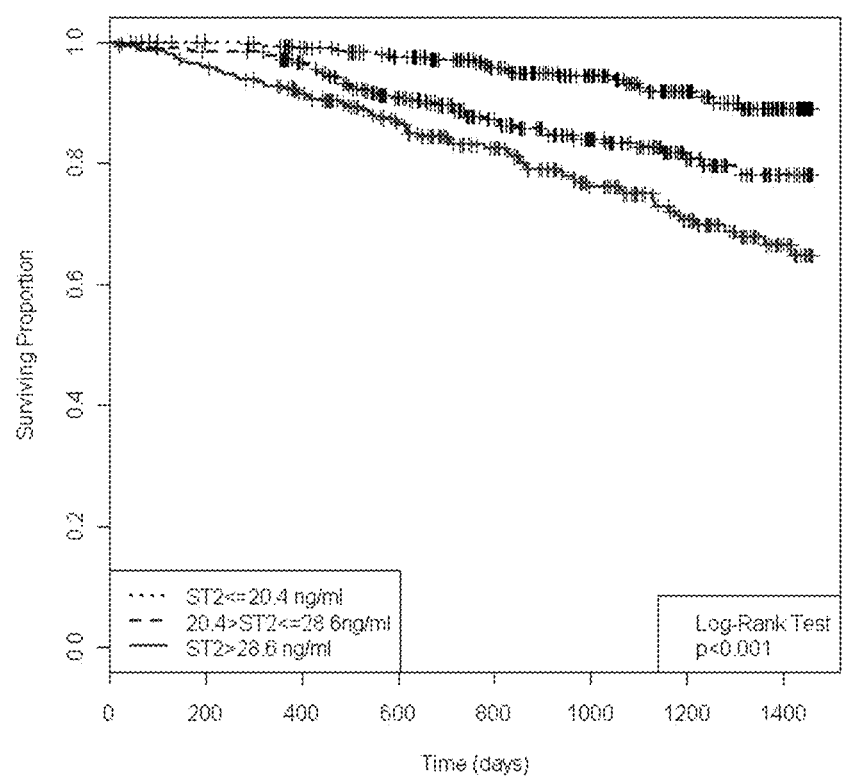
FIG. 1 is a Kaplan-Meier graph showing the surviving proportion of heart failure subjects over time within the identified groups. The survival data for subjects having a soluble ST2 level less than or equal to 20.4 ng/mL (top line); greater than 20.4 ng/mL, but less than or equal to 28.6 ng/mL (middle line); and greater than 28.6 ng/mL (bottom line) are shown (log-rank test, p<0.001).

Provided herein are methods of treating a subject having a cardiovascular disease; selecting a therapy for a subject having a cardiovascular disease; identifying a subject that will benefit or will not benefit from exercise therapy; determining whether a subject having a cardiovascular disease should begin, continue, or discontinue exercise therapy; and predicting the efficacy of exercise therapy in a subject having a cardiovascular disease. Also provided are methods of reducing the risk an adverse outcome (e.g., death) in a subject having a cardiovascular disease. These methods require determining a level of soluble ST2 in a biological sample from the subject.

Cardiovascular Diseases

A cardiovascular disease is a disorder of the heart and blood vessels (e.g., disorders of the arteries, veins, arterioles, venules, and capillaries). Cardiovascular diseases can be diagnosed using methods known in the art. Non-limiting examples of cardiovascular disease include congestive heart failure, stroke, acute coronary artery disease, arrhythmia, asymmetric septal hypertrophy (e.g., left ventricular hypertrophy with resultant diastolic dysfunction), cardiomyopathy, valvular dysfunction, pericarditis, atherosclerosis, and myocardial infarction. A subject can be diagnosed as having a cardiovascular disease by a medical professional (e.g., a physician, a physician's assistant, a nurse, a nurse's assistant, or a laboratory technician) using exemplary methods described herein. Additional methods for diagnosing a cardiovascular disease are known in the art.

Heart failure is a clinical syndrome of diverse etiologies linked by the common feature of impaired heart pumping and characterized by the failure of the heart to pump blood commensurate with the requirements of the metabolizing tissues. Heart failure can be diagnosed in a subject by the observation of one or more of the following non-limiting symptoms in a subject: dyspnea, fatigue and weakness, edema in the legs, ankles, and feet, rapid or irregular heartbeat, reduced ability to exercise, persistent cough or wheezing, white or pink blood-tinged phlegm, abdominal swelling (ascites), sudden weight gain from fluid retention, lack of appetite, nausea, difficulty concentrating or decreased alertness, and chest pain. Additional non-limiting methods for diagnosing heart failure in a subject include the use of commercially available diagnostic tests (e.g., enzyme-linked immunosorbent assays) known in the art.

A myocardial infarction is a focus of necrosis resulting from inadequate perfusion of the cardiac tissue. Myocardial infarction generally occurs from an abrupt decrease in coronary blood flow that follows a thrombotic occlusion of a coronary artery previously narrowed by atherosclerosis. Generally, a myocardial infarction occurs when an atherosclerotic plaque fissures, ruptures, or ulcerates, and a mural thrombus forms leading to coronary artery occlusion. Non-limiting methods of diagnosing a myocardial infarction include the use of a number of commercially available diagnostic tests known in the art. Generally, these diagnostic tests may be divided into four main categories: (1) nonspecific indexes of tissue necrosis and inflammation; (2) electrocardiograms; (3) serum enzyme changes (e.g., creatine phosphokinase levels); and (4) cardiac imaging. A myocardial infarction can also be diagnosed by the observation of one or more of the following symptoms in a subject: chest pain (typically on the left side of the body), neck or jaw pain, shoulder or arm pain, clammy skin, dyspnea, nausea, and vomiting. Additional methods of diagnosing a myocardial infarction are known in the art.

A stroke can be diagnosed in a subject by the observation of one or more symptoms and/or by a physical examination (e.g., interventional and non-interventional diagnostic tools, such as computed tomography and magnetic resonance imaging). Non-limiting symptoms of a stroke include: paralysis, weakness, decreased sensation and/or vision, numbness, tingling, aphasia (e.g., inability to speak or slurred speech, or difficulty reading or writing), agnosia (i.e., inability to recognize or identify sensory stimuli), loss of memory, coordination difficulties, lethargy, sleepiness or unconsciousness, lack of bladder or bowel control, and cognitive decline (e.g., dementia, limited attention span, and inability to concentrate). In some examples, medical imaging techniques can be used identify a subject having an infarct or a hemorrhage in the brain.

Cardiac hypertrophy is typically characterized by left ventricular hypertrophy, usually of a non-dilated chamber, that occurs without an obvious antecedent cause. Cardiac hypertrophy can be diagnosed through the use of electrocardiography or echocardiography.

Arteriosclerosis is a cardiovascular disease characterized by a hardening or loss of elasticity. Arteriosclerosis can be diagnosed by the detection of one or more of the following physical symptoms: a weak or absent pulse below the narrowed area of an artery, decreased blood pressure in an affected limb, bruits caused by turbulent flow in an artery, an aneurysm in the abdomen or behind the knee, poor wound healing, and increased levels of cholesterol. Atherosclerosis can also be detected using imaging techniques including, but not limited to: Doppler ultrasound, electrocardiography, angiography, computed tomography, or magnetic resonance (e.g., magnetic resonance angiography).

A subject can be diagnosed as having a cardiovascular disease following admission to a hospital or following presentation to a health care clinic. Effective therapeutic treatment of a cardiovascular disease can be determined by observing a decrease in the number of symptoms of a cardiovascular disease in a subject or a decrease in the frequency, intensity, and/or duration of one or more symptoms of a cardiovascular disease (e.g., any of the symptoms described herein) in a subject. Effective therapeutic treatment of a cardiovascular disease can also be determined by detecting a decrease in the levels of one or more markers of a cardiovascular disease (e.g., any of the markers of cardiovascular disease known in the art or described herein) in a biological sample from a subject over time (e.g., a significant decrease in the level of at least one marker at a second time point compared to the level of the biomarker at a first time point prior to the start of treatment or at an earlier time point during the treatment period). Successful treatment of a cardiovascular disease can also be determined by a decreased risk of an adverse event (e.g., a decreased risk of death, hospitalization or rehospitalization, organ failure, organ transplantation, or a first or subsequent myocardial infarction) (e.g., compared to the risk of an adverse event in patient population diagnosed with the same cardiovascular disease but receiving no treatment or a different treatment).

Exercise Therapy

Subjects diagnosed as having a cardiovascular disease are often directed/instructed by a healthcare provider to perform an exercise therapy regime. Exercise therapy is a treatment regime that involves the periodic performance of physical activity by a subject (e.g., a subject diagnosed as having a cardiovascular disease). The physical activity performed during this type of therapy can be aerobic (e.g., walking, jogging/running, swimming, biking, or rowing) or anaerobic (e.g., weight lifting or resistance training) exercise. The physical activity can be performed in the presence of a health care professional (e.g., a physical therapist, a nurse, a nurse's assistant, a physician's assistant, or a physician). The physical activity can be performed at least once a week (e.g., at least once a day, twice a day, two times a week, three times a week, four times a week, five times a week, or six times a week). In some embodiments, a single episode of physical activity within the exercise therapy regime can last between 5 minutes and 3 hours, between 5 minutes and 2 hours, between 5 minutes and 1 hour, or between 10 minutes and 1 hour. The intensity and/or type of the physical activity performed by the subject can vary with the physical condition of the subject (e.g., age, severity of cardiovascular disease, additional disease states, weight, and blood pressure). A subject can continue to perform an exercise therapy regime over an extended period of time (e.g., over a period of 1 month to 1 year, 1 month to 2 years, 1 year to 3 years, 2 years to 5 years, or 4 years to 10 years). In some embodiments, a subject can be monitored by a health care professional to adjust one or more parameters of the exercise therapy regime, including the frequency, intensity, length of individual episodes of physical activity, and the type of physical activity performed. The efficacy of exercise therapy in a subject having a cardiovascular disease can be determined using any of the methods for determining successful treatment of a cardiovascular disease (e.g., those methods described herein or known in the art). A subject can continue to perform an exercise therapy regime until instructed by a health care professional to discontinue the exercise therapy or until a specific therapeutic outcome has been achieved (e.g., a decrease in the number of symptoms of a cardiovascular disease has been achieved, a decrease in severity, intensity, or frequency of one or more symptoms of a cardiovascular disease has been achieved, or a decrease in the levels of one or more markers of a cardiovascular disease has been achieved in the subject).

ST2

The ST2 gene is a member of the interleukin-1 receptor family whose protein product exists both as a trans-membrane form as well as a soluble receptor that is detectable in serum (Kieser et al., *FEBS Lett.* 372(2-3):189-193, 1995; Kumar et al., *J Biol. Chem.* 270(46):27905-27913, 1995; Yanagisawa et al., *FEBS Lett.* 302(1):51-53, 1992; Kuroiwa et al., *Hybridoma* 19(2):151-159, 2000). Soluble ST2 was described to be markedly up-regulated in an experimental model of heart failure (Weinberg et al., *Circulation* 106(23): 2961-2966, 2002), and data suggest that human soluble ST2 concentrations are also elevated in those with chronic severe heart failure (Weinberg et al., *Circulation* 107(5):721-726, 2003), as well as in those with acute myocardial infarction (Shimpo et al., *Circulation* 109(18):2186-2190, 2004).

Without wishing to be bound by theory, the transmembrane form of ST2 is thought to play a role in modulating responses of T helper type 2 cells (Lohning et al., *Proc. Natl. Acad. Sci. U.S.A.* 95(12):6930-6935, 1998; Schmitz et al., *Immunity* 23(5):479-490, 2005), and may play a role in development of tolerance in states of severe or chronic inflammation (Brint et al., *Nat. Immunol.* 5(4):373-379, 2004), while the soluble form of ST2 is up-regulated in growth stimulated fibroblasts (Yanagisawa et al., 1992, supra). Experimental data suggest that the ST2 gene is markedly up-regulated in states of cardiomyocyte stretch (Weinberg et al., 2002, supra) in a manner analogous to the induction of the BNP gene (Bruneau et al., *Cardiovasc. Res.* 28(10):1519-1525, 1994).

Tominaga et al. (*FEBS Lett.* 258:301-304, 1989) isolated murine genes that were specifically expressed by growth stimulation in BALB/c-3T3 cells. Haga et al. (*Eur J. Biochem.* 270:163-170, 2003) describes that the ST2 gene was named on the basis of its induction by growth stimulation. The ST2 gene encodes two protein products: ST2 or sST2, which is a soluble secreted form, and ST2L, a transmembrane receptor form that is very similar to the interleukin-1 receptors. The HUGO Nomenclature Committee designated the human homolog of ST2, the cloning of which was described in Tominaga et al., *Biochim. Biophys. Acta.* 1171:215-218, 1992, as Interleukin 1 Receptor-Like 1 (IL1RL1). The two terms are used interchangeably in the art.

The mRNA sequence of the shorter, soluble isoform of human ST2 can be found at GenBank Acc. No. NM_003856.2 (SEQ ID NO: 2), and the polypeptide sequence is at GenBank Acc. No. NP_003847.2 (SEQ ID NO: 1). The mRNA sequence for the longer form of human ST2 is at GenBank Acc. No. NM_016232.4 (SEQ ID NO: 4), and the polypeptide sequence is at GenBank Acc. No. NP_057316.3 (SEQ ID NO: 3). Additional information is available in the public databases at GeneID: 9173, MIM ID #601203, and UniGene No. Hs.66.

Methods for detecting and measuring soluble ST2 are known in the art, e.g., as described in U.S. Patent Application Publication Nos. 2003/0124624, 2004/0048286, and 2005/0130136, and U.S. patent application Ser. No. 13/083, 333 and PCT Application No. PCT/US2011/031801, the entire contents of which are incorporated herein by reference. These U.S. patent application publications describe methods of determining the level of soluble ST2 using an antibody or antibody fragment that binds to soluble ST2. Kits for measuring soluble ST2 are also commercially available, e.g., the ST2 ELISA Kit manufactured by Medical & Biological Laboratories Co., Ltd. (MBL International Corp., Woburn, Mass.), No. 7638. In addition, devices for measuring ST2 and other biomarkers are described in U.S. Patent Application Publication No. 2005/0250156 (incorporated herein by reference in its entirety).

As described in detail herein, soluble ST2 levels can be determined in any biological sample from a subject, including blood, serum, plasma, urine, and body tissue. Generally, the level of soluble ST2 is determined in a sample containing serum, blood, or plasma. The level of soluble ST2 can be determined in a biological sample that has been stored for a period of time (e.g., for at least 1 hour, 1 day, 1 week, or 1 month) at a temperature at or below 10° C. (e.g., below 0° C., below −20° C., or around −196° C.).

Elevated concentrations of soluble ST2 are markedly prognostic for death in patients with heart failure, with a dramatic divergence in survival curves for those with elevated soluble ST2 soon after presentation (Weinberg et al., *Circulation* 107:721-726, 2003; Mueller et al., *Clin Chem.* 54(4):752-756, 2008; Daniels et al., *Am. Heart J.* 160:721-728, 2010; Ky et al., *Circ. Heart Fail.* 4(2):180-187, 2011; and Manzano-Fernandez et al., *Am. J. Cardiol.* 107:259-267, 2011). The relationship between soluble ST2 and death in heart failure patients was shown to be independent of etiology, and superseded all other biomarker predictors of mortality in this setting, including other markers of inflammation, myonecrosis, renal dysfunction, and most notably NT-proBNP, a marker well known as having value for predicting death in heart failure patients.

Reference Levels of ST2

As described herein, the level of soluble ST2 in a subject indicates whether a subject having a cardiovascular disease should be selected for exercise therapy, whether a subject will benefit or will not benefit from exercise therapy, or whether a subject should begin, continue, or discontinue exercise therapy. In addition, the level of soluble ST2 in a subject can be used to select a therapy including exercise for a subject having a cardiovascular disease. Additional clinical and therapeutic uses of detecting a level of soluble ST2 are described herein and are known in the art. Reference levels of human soluble ST2 can be determined using methods known in the art (e.g., using the antibodies described in U.S. patent application Ser. No. 13/083,333 and PCT Application No. PCT/US2011/031801). In general, it will be desirable to use a reference level of soluble ST2 determined using the same method as is used to determine the level of soluble ST2 in the subject.

Risk Reference Levels

The methods described herein can include comparing the level of soluble ST2 in a biological sample to a reference level of soluble ST2. A reference level of soluble ST2 can be or represent a level of soluble ST2 found in a biological sample from a subject (e.g., a control subject who experienced or was more likely to experience an adverse outcome and engaged in exercise) or a population (e.g., a population of subjects who experienced or were more likely to experience an adverse outcome and engaged in exercise), or can be or represent a threshold level of soluble ST2 above which the risk of an adverse outcome is increased in those who engage in exercise therapy. These reference levels are referred to herein as the "risk reference level." In general, the presence of a level of ST2 below the risk reference level indicates that the subject does not have an elevated risk of an adverse outcome if they engage in exercise therapy, while the presence of a level of ST2 above the risk reference level indicates that the subject has an elevated risk of an adverse outcome if they do engage in exercise therapy.

In some embodiments, the risk reference level of soluble ST2 is a threshold level of soluble ST2 or a percentile (e.g., 75th, 80th, 85th, 90th, or 95th percentile) of soluble ST2 levels in a population of subjects who experienced an adverse outcome and engaged in exercise.

In some embodiments, efficacy reference level is about 55 ng/mL, determined using the Presage ST2 kit, or the equivalent thereof.

Efficacy Reference Levels

Alternatively or in addition, the methods described herein can include comparing the level of soluble ST2 in a biological sample to a reference level of soluble ST2 that is or represents a level of soluble ST2 found in a biological sample from a subject (e.g., a control subject who experienced a therapeutic benefit from exercise therapy, i.e., did not or was less likely to experience an adverse outcome and engaged in exercise) or a population (e.g., a population of subjects who experienced a therapeutic benefit from exercise therapy, i.e., did not experience or were less likely to experience an adverse outcome and engaged in exercise), or can be or represent a threshold level of soluble ST2 below which the subject is likely to experience a therapeutic benefit from exercise therapy, i.e., a threshold level of soluble ST2 below which the likelihood of an adverse outcome is decreased in those who engage in exercise therapy. These reference levels are referred to herein as the "efficacy reference level." In general, the presence of a level of ST2 below the efficacy reference level indicates that the subject has an increased likelihood of not experiencing an adverse outcome if they engage in exercise therapy, while the presence of a level of ST2 above the efficacy reference level indicates that the subject has an elevated risk of an adverse outcome if they do engage in exercise therapy.

In some embodiments, the efficacy reference level of soluble ST2 is a threshold level of soluble ST2 or a percentile (e.g., 75th, 80th, 85th, 90th, or 95th percentile) of soluble ST2 levels in a population of subjects who experienced an adverse outcome and engaged in exercise.

In some embodiments, efficacy reference level is about 35 ng/mL, determined using the Presage ST2 kit, or the equivalent thereof.

Healthy Controls and Other Reference Levels

In some embodiments, the methods described herein can also include comparing the level of soluble ST2 in a biological sample to a reference level of soluble ST2 that represent the average level of soluble ST2 present in a population of subjects: a population of subjects diagnosed as having a specific cardiovascular disease, a population of healthy subjects not diagnosed with a disease (e.g., a healthy male patient population or a healthy female patient population), a population of subjects not at risk of developing a cardiovascular disease, or a population of subjects not presenting with two or more symptoms of a cardiovascular disease. A reference level can also be a baseline level or a level in the same patient measured at an earlier or later point in time. Additional non-limiting examples of reference levels of human soluble ST2 include the level of human soluble ST2 in a subject or a patient population that: does not have high risk cardiovascular disease; does not have renal failure; does not have hypertriglyceridemia, hypercholesterolemia, hypertension, and/or a body mass index of <30 (e.g., a BMI under 25); and/or does not suffer from a pulmonary disease, sepsis, or Kawasaki disease.

In some embodiments, the reference level of soluble ST2 is a threshold level of soluble ST2. In some embodiments, the threshold level of soluble ST2 is a median level of soluble ST2 or a percentile (e.g., 75th, 80th, 85th, 90th, or 95th percentile) of soluble ST2 levels in a healthy patient population, e.g., a healthy male patient population or a healthy female patient population (e.g., any of the values or ranges listed in Table 1).

TABLE 1 sST2 Concentrations at Specific Thresholds - US Self-Reported Healthy Cohort[1]

| Per-centiles | Entire Cohort | | Male | | Female | |
|---|---|---|---|---|---|---|
| | ST2 (ng/mL) | 95% CI | ST2 (ng/mL) | 95% CI | ST2 (ng/mL) | 95% CI |
| 2.5 | 8.0 | 7.1 to 8.6 | 8.6 | 7.7 to 11.8 | 7.3 | 5.5 to 8.4 |
| 5 | 9.3 | 8.4 to 10.2 | 11.8 | 8.6 to 12.7 | 8.5 | 7.3 to 9.4 |
| 10 | 11.5 | 10.3 to 11.9 | 13.7 | 12.2 to 14.8 | 10.2 | 9.0 to 11.2 |
| 25 | 14.5 | 13.7 to 15.2 | 17.6 | 16.8 to 18.7 | 12.4 | 11.9 to 13.5 |
| median | 18.8 | 18.2 to 19.9 | 23.6 | 21.3 to 25.1 | 16.2 | 15.4 to 17.4 |
| 75 | 25.3 | 23.8 to 26.9 | 30.6 | 28.7 to 33.3 | 19.9 | 18.8 to 20.8 |
| 90 | 34.3 | 32.4 to 35.6 | 37.2 | 35.5 to 40.9 | 23.7 | 22.2 to 25.8 |
| 95 | 37.9 | 35.9 to 41.3 | 45.4 | 39.4 to 48.6 | 29.0 | 24.6 to 33.2 |
| 97.5 | 45.6 | 40.1 to 48.7 | 48.5 | 45.8 to 58.5 | 33.1 | 29.6 to 39.9 |

[1]These levels were determined using the antibodies described in U.S. patent application Ser. No. 13/083,333 and PCT Application No. PCT/US2011/031801.

In some embodiments, the threshold level is 28.6 ng/mL, about 28 ng/mL to about 35 ng/mL, 35 ng/mL, about 35 ng/mL to about 45 ng/mL, about 45 ng/mL to about 55 ng/mL, or the range of 55 to 60 ng/mL (e.g., the entire range or any level between 55 to 60 ng/mL) (e.g., using the antibodies described in U.S. patent application Ser. No. 13/083,333 and PCT Application No. PCT/US2011/031801). Reference levels of human soluble ST2 can be determined using methods known in the art (e.g., using the antibodies described in U.S. patent application Ser. No. 13/083,333 and PCT Application No. PCT/US2011/031801). Additional reference levels of soluble ST2 are known in the art. As is known in the art, the reference level of soluble ST2 can vary based on the assay used to determine soluble ST2 levels.

Subjects

The methods described herein can be performed on a variety of subjects having a cardiovascular disease (e.g., any of the subjects described herein). In some embodiments of any of the methods, the subject has been previously diagnosed as having a cardiovascular disease. In some embodiments of any of the methods, the subject is hyperchlosterolemic, hypertriglyceridemic, hyperlidemic, a smoker, hypertensive, or has a body mass index of greater than 25 (e.g., between 25 and 30, or greater than 30). In some embodiments of any of the methods, the subject can already be receiving a therapeutic agent (e.g., one or more of the additional therapeutic agents described herein or known in the art for treating a cardiovascular disease). In some embodiments, the subject has heart failure.

In some embodiments of any of the methods, the subject can have previously been admitted to a hospital or can be receiving treatment on an outpatient basis. In some embodiments of any of the methods, the patient can be 20 to 40 years old, 40 to 50 years old, 50 to 60 years old, 60 to 70 years old, 70 to 80 years old, 80 to 90 years old, or 90 to 100 years old.

Methods of Treating a Subject Having a Cardiovascular Disease

Provided herein are methods of treating a subject having a cardiovascular disease (e.g., any of the cardiovascular diseases described herein or known in the art, e.g., heart failure). These methods include determining a level of soluble ST2 in a biological sample from the subject, identifying a subject that has a decreased (e.g., a significant or detectable decrease) level of soluble ST2 in the biological sample compared to a risk or efficacy reference level of soluble ST2 (e.g., as described herein), and selecting the identified subject for exercise therapy (e.g., any form of exercise therapy described herein or known in the art). Also provided are methods of treating a subject that include determining a level of soluble ST2 in a biological sample from the subject, identifying a subject that has an increased (e.g., a significant or detectable increase) level of soluble ST2 in the biological sample compared to a risk or efficacy reference level of soluble ST2 (e.g., as described herein), and instructing the identified subject not to begin, to discontinue, or to avoid exercise therapy. The level of soluble ST2 in the biological sample can be determined using any of the methods described herein (e.g., methods using an antibody or antibody fragment that binds specifically to soluble ST2). The biological sample can be any of the biological samples described herein. In some embodiments, the biological sample is collected from a subject within 2 or 4 years of diagnosis with a cardiovascular disease, a myocardial infarction, or heart failure.

The selected subject can begin performance of any of the exercise therapy regimes described herein. Some embodiments of these methods further include monitoring the subject to determine whether the exercise therapy regime should be continued or altered in one or more aspects (e.g., any of the aspects of exercise therapy regimes described herein). Methods for monitoring the subject to determine whether the exercise therapy should be continued or discontinued are described herein. These methods can be performed by any health care professional (e.g., a physician, a physical therapist, a nurse, a physician's assistant, a laboratory technician, or a nursing assistant).

In some embodiments, the treating results in a reduced (e.g., a significant decrease) in the risk of an adverse outcome (e.g., any of the adverse outcomes described herein) in the subject. In some embodiments, the treating results in a decrease in the number of symptoms of a cardiovascular disease, a decrease (e.g., a significant or detectable decrease) in the intensity, frequency, or duration of one or more symptoms of a cardiovascular disease, or a decrease in the level of at least one marker of a cardiovascular disease in a biological sample from the subject.

Methods of Selecting a Therapy for a Subject Having a Cardiovascular Disease

Also provided are methods of selecting a therapy for a subject having a cardiovascular disease. These methods include determining a level of soluble ST2 in a biological sample from the subject and comparing the level of soluble ST2 in the biological sample to a risk or efficacy reference level of soluble ST2 (e.g., any of the reference levels of soluble ST2 described herein or known in the art), where a decreased (e.g., a significant or detectable decrease) level of soluble ST2 in the biological sample compared to the risk or efficacy reference level of soluble ST2 indicates that the subject should begin or continue exercise therapy (e.g., any of the exercise therapy regimes described herein), and an elevated (e.g., a significant or detectable increase) level of soluble ST2 in the biological sample compared to the risk or efficacy reference level of soluble ST2 indicates that the subject should not begin or should discontinue exercise therapy. The level of soluble ST2 in the biological sample can be determined using any of the methods described herein, and the biological sample can be any of the biological samples described herein. In some embodiments, the biological sample is collected from a subject within 2 or 4 years of diagnosis with a cardiovascular disease, a myocardial infarction, or heart failure. These methods can be performed by any health care professional (e.g., a physician, a physical therapist, a nurse, a physician's assistant, a laboratory technician, or a nursing assistant). In some embodiments, the subject can already be performing an exercise therapy regime.

Methods of Identifying a Subject that Will Benefit/not Benefit from Exercise Therapy Also provided herein are methods for identifying a subject that will benefit from exercise therapy (benefit from the performance of any of the exercise therapy regimes described herein). The methods include determining a level of soluble ST2 in a biological sample from the subject, and selecting a subject that has a decreased (e.g., a significant or detectable decrease) level of soluble ST2 in the biological sample compared to an efficacy reference level of soluble ST2 (e.g., any of the reference levels of soluble ST2 described herein or known in the art), where the selected subject is identified as a subject that will benefit from exercise therapy (e.g., any of the exercise therapy regimes described herein). Also provided are methods of identifying a subject that will not benefit from exercise therapy (will not benefit from the performance of any of the exercise therapy regimes described herein) that include determining a level of soluble ST2 in a biological sample from the subject, and selecting a subject that has an elevated (e.g., a significant or detectable increase) level of soluble ST2 in the biological sample compared to an efficacy reference level of soluble ST2 (e.g., any of the reference levels of soluble ST2 described here in or known in the art), where the selected subject is identified as a subject that will not benefit from exercise therapy (e.g., any of the exercise therapy regimes described herein).

In some embodiments, the biological sample is collected from a subject within 2 or 4 years of diagnosis with a cardiovascular disease, a myocardial infarction, or heart failure. In some embodiments, the efficacy reference level of soluble ST2 is a threshold soluble ST2 level of less than or equal to 35 ng/mL or a range of 55 to 60 ng/mL (e.g., the entire range or any level between 55 to 60 ng/mL). The level of soluble ST2 in the biological sample can be determined using any of the methods described herein (e.g., methods using an antibody or antibody fragment that binds specifically to soluble ST2), and the biological sample can be any of the biological samples described herein.

In some embodiments of these methods, the subject has been previously diagnosed as having a cardiovascular disease (e.g., previously diagnosed as having heart failure). In some embodiments, the subject is hyperchlosterolemic, hypertriglyceridemic, hyperlidemic, a smoker, hypertensive, or has a body mass index of greater than 25 (e.g., between 25 and 30, or greater than 30). In some embodiments, the subject can already be receiving a therapeutic agent (e.g., one or more of the additional therapeutic agents described herein or known in the art for treating a cardiovascular disease). In some embodiments, the subject can have previously been admitted to a hospital or can be receiving treatment on an outpatient basis. In some embodiments, the patient can be 20 to 40 years old, 40 to 50 years old, 50 to 60 years old, 60 to 70 years old, 70 to 80 years old, 80 to 90 years old, or 90 to 100 years old.

In some embodiments, the benefit from exercise therapy can be one or more of the following: a reduction (e.g., a significant decrease) in the risk of an adverse outcome (e.g., any of the adverse outcomes described herein) in the subject, a reduction in the number of symptoms of a cardiovascular disease, a reduction (e.g., a detectable or observable decrease) in the intensity, frequency, or duration of one or more symptoms of a cardiovascular disease, or a reduction (e.g., detectable decrease) in the levels of at least one marker of a cardiovascular disease in a biological sample from the subject (e.g., as compared to a subject or population of subjects having the same cardiovascular disease but not receiving therapy or receiving a different therapy). The benefit from exercise therapy can be determined at various time points in a subject (e.g., after at least 6 months of exercise therapy, after 1 year of exercise therapy, or after 2 years of exercise therapy).

Methods of Determining Whether a Subject should Begin, Continue, or Discontinue Exercise Therapy Also provided are methods of determining whether a subject having a cardiovascular disease should begin or continue exercise therapy (e.g., any of the exercise therapy regimes described herein) that include determining a level of soluble ST2 in a biological sample from the subject, wherein a decreased (e.g., a significant or detectable decrease) level of soluble ST2 in the biological sample compared to a risk or efficacy reference level of soluble ST2 (e.g., any of the reference levels described herein) indicates that the subject should begin or continue exercise therapy. Also provided are methods of determining whether a subject having a cardiovascular disease should not begin or discontinue exercise therapy (e.g., any of the exercise therapy regimes described herein) that include determining a level of soluble ST2 in a biological sample from the subject, where an elevated (e.g., a significant or detectable increase) level of soluble ST2 in the biological sample compared to a risk or efficacy reference level of soluble ST2 (e.g., any of the reference levels of soluble ST2 described herein) indicates that the subject should not begin or discontinue exercise therapy.

Also provided are methods of determining whether a subject having a cardiovascular disorder should discontinue or avoid exercise therapy (e.g., any of the exercise therapy regimes described herein) that include determining a level of soluble ST2 in a biological sample from the subject at a first time point before or after the start of exercise therapy, and determining a level of soluble ST2 in a biological sample from the subject undergoing (performing) exercise therapy at a second time point after the start of exercise therapy and after the first time point, where an increase (e.g., a significant or detectable increase) in the level of soluble ST2 in the biological sample of the second time point compared to the level of soluble ST2 in the biological sample at the first time point indicates that the subject should discontinue or avoid exercise therapy. Also provided are methods of determining whether a subject having a cardiovascular disorder should continue exercise therapy (e.g., any of the exercise therapy regimes described herein) that include determining a level of soluble ST2 in a biological sample from the subject at a first time point before or after the start of exercise therapy, and determining a level of soluble ST2 in a biological sample from the subject undergoing (performing) exercise therapy at a second time point after the start of exercise therapy and after the first time point, where a decrease (e.g., a significant or detectable decrease) or no change (e.g., no significant change) in the level of soluble ST2 in the biological sample of the second time point compared to the level of soluble ST2 in the biological sample at the first time point indicates that the subject should continue exercise therapy.

Also provided are methods of determining whether a subject having a cardiovascular disorder should continue exercise therapy (e.g., any of the exercise therapy regimes described herein) that include determining a level of soluble ST2 in a biological sample from the subject at a first time point before or after the start of exercise therapy, and instructing the subject to begin or continue exercise therapy if the level of soluble ST2 is below a risk or efficacy reference level; and determining a level of soluble ST2 in a biological sample from the subject undergoing (performing) exercise therapy at a second time point after the start of exercise therapy and after the first time point, and instructing the subject to continue the exercise therapy if the level at the second time point is still below the risk or efficacy reference level, or to stop the exercise therapy if the level at the second time point is above the risk or efficacy reference level.

In some embodiments, one or more additional levels of soluble ST2 can be determined in the subject (e.g., determined in biological samples obtained at one or more additional time points after the second time point). In some embodiments, the level of soluble ST2 is determined in a biological sample obtained from the subject having cardiovascular disease at least every month (e.g., at least every two months, at least every three months, at least every four months, at least every five months, or at least every six months) during the performance of a exercise therapy regime. In such embodiments, an increase (e.g., a significant or detectable increase) in the level of soluble ST2 in a biological sample taken at a later time point compared to the level of soluble ST2 in a biological sample taken at an earlier time point (e.g., the immediately prior biological sample), or the presence of a level above a risk or efficacy reference level, indicates that the subject should discontinue exercise therapy, and a decrease (e.g., a significant or detectable decrease) or no change (e.g., no significant change) in the level of soluble ST2 in a biological sample taken at a later time point compared to the level of soluble ST2 in a biological sample taken at an earlier time point (e.g., the immediately prior biological sample), or the presence of a level below a risk or efficacy reference level, indicates that the subject should continue exercise therapy. In some embodiments of these methods, the subjects are monitored by a health care professional (e.g., a physician, a physical therapist, a nurse, a nurse's assistant, a physician's assistant, or a laboratory technician).

In some embodiments, the biological sample is collected from a subject within 2 years of diagnosis with a cardiovascular disease, a myocardial infarction, or heart failure. The level of soluble ST2 in the biological sample can be determined using any of the methods described herein, and the biological sample can be any of the biological samples described herein. These methods can reduce (e.g., a significant reduction) in the risk of death or an adverse outcome (e.g., any of the adverse outcomes described herein) in the subject, reduce the number of symptoms of a cardiovascular disease, reduce (e.g., a detectable or observable reduction) in the intensity, frequency, or duration in one or more symptoms of a cardiovascular disease, or reduce (e.g., detectable reduction) in the level of at least one marker (e.g., any of the markers described herein) of a cardiovascular disease in a biological sample from the subject (e.g., as compared to a subject or population of subjects having the same cardiovascular disease but not receiving therapy or receiving a different therapy).

Methods of Reducing the Risk of an Adverse Outcome in a Subject

Also provided herein are methods of reducing (e.g., a significant reduction) the risk of an adverse outcome (e.g., risk of death) in a subject having a cardiovascular disease that include determining a level of soluble ST2 in a biological sample from the subject, identifying a subject that has a decreased (e.g., a significant or detectable decrease) level of soluble ST2 in the biological sample compared to a risk reference level of soluble ST2 (e.g., as described herein), and selecting the identified subject for exercise therapy (e.g., any of the exercise therapy regimes described herein). Also provided are methods of reducing (e.g., a significant reduction) the risk of an adverse outcome (e.g., risk of death) in a subject having a cardiovascular disease that include determining a level of soluble ST2 in a biological sample from the subject, identifying a subject that has an elevated (e.g., a significant or detectable increase) level of soluble ST2 in the biological sample compared to a risk reference level of soluble ST2 (e.g., as described herein), and instructing the identified subject to avoid or discontinue exercise therapy (e.g., any of the exercise therapy regimes described herein).

In some embodiments, the adverse outcome can be one or more of: death, organ failure, organ transplantation, hospitalization or rehospitalization, recurrence of one or more symptoms of a cardiovascular disease, development of one or more additional symptoms of a cardiovascular disease, an increase in the frequency, intensity, or duration of one or more symptoms of a cardiovascular disease experienced by the subject, or a first or subsequent myocardial infarction. In some embodiments, the biological sample is collected from a subject within 2 years of diagnosis with a cardiovascular disease, a myocardial infarction, or heart failure. Any of these methods can be performed by a health care professional (e.g., a physician, a physical therapist, a nurse, a nurse's assistant, a physician's assistant, or a laboratory technician).

Methods of Predicting the Efficacy of Exercise Therapy

Also provided are methods of predicting the efficacy of exercise therapy (e.g., any of the exercise therapy regimes described herein) in a subject having a cardiovascular disease. These methods include determining a level of soluble ST2 in a biological sample from the subject, and comparing the level of soluble ST2 in the biological sample to an efficacy reference level of soluble ST2 (e.g., any of the reference levels of soluble ST2 described herein), wherein a decreased (e.g., a significant or detectable decrease) level of soluble ST2 in the biological sample compared to the efficacy reference level of soluble ST2 (e.g., as described herein) indicates that exercise therapy will be effective in the subject, and an elevated (e.g., a significant or detectable increase) level of soluble ST2 in the biological sample compared to the efficacy reference level of soluble ST2 (e.g., as described herein) indicates that the exercise therapy will not be effective in the subject. In some embodiments, the efficacy reference level of soluble ST2 is a threshold soluble ST2 level of 28.6 ng/mL, less than or equal to 35 ng/mL, about 28 ng/mL to about 35 ng/mL (e.g., the entire range or any level between 28 to 35 ng/mL), 35 ng/mL, about 35 ng/mL to about 45 ng/mL (e.g., the entire range or any level between 35 to 45 ng/mL), about 45 ng/mL to about 55 ng/mL (e.g., the entire range or any level between 45 to 55 ng/mL), about 35 ng/mL to about 55 ng/mL (e.g., the entire range or any level between 35 to 55 ng/mL), or the range of 55 to 60 ng/mL (e.g., the entire range or any level between 55 to 60 ng/mL) (e.g., determined using the antibodies described in U.S. patent application Ser. No. 13/083,333 and PCT Application No. PCT/US2011/031801). In some embodiments, the biological sample is collected from a subject within 2 years of diagnosis with a cardiovascular disease, a myocardial infarction, or heart failure. The level of soluble ST2 in the biological sample can be determined using any of the methods described herein, and the biological sample can be any of the biological samples described herein.

In some embodiments, the efficacy of exercise therapy can be one or more of the following: a reduction (e.g., a significant decrease) in the risk of an adverse outcome (e.g., any of the adverse outcomes described herein) in the subject, a reduction in the number of symptoms of a cardiovascular disease, a reduction (e.g., a detectable or observable decrease) in the intensity, frequency, or duration of one or more symptoms of a cardiovascular disease, or a reduction (e.g., detectable decrease) in the levels of at least one marker of a cardiovascular disease (e.g., any of the markers described herein or known in the art) in a biological sample from the subject (e.g., as compared to a subject or population of subjects having the same cardiovascular disease but not receiving therapy or receiving a different therapy). The efficacy of exercise therapy can be determined at various time points in a subject (e.g., after at least 6 months of exercise therapy, after 1 year of exercise therapy, or after 2 years of exercise therapy).

Additional Therapeutic Markers

Any of the methods described herein can further include determining the level of at least one additional marker (e.g., at least one additional marker of a cardiovascular disease) in a biological sample from a subject. In some embodiments, the biological sample used to determine the level of the at least one additional marker may be the same sample(s) that is used to determine a level of soluble ST2 in a subject. In some embodiments, the biological sample used to determine the level of the at least one additional marker is a different sample than the sample(s) used to determine a level of soluble ST2 in a subject. The biological sample can be any of the biological samples described herein.

The additional marker can be any protein, nucleic acid, lipid, or carbohydrate, or a combination (e.g., two or more) thereof, that is diagnostic of the presence of a particular disease (e.g., diagnostic of a cardiovascular disease). Several additional markers useful for the diagnosis of a cardiovascular disease are known in the art, and include, without limitation, cardiac troponin I, B-type natriuretic peptide (e.g., proBNP, NT-proBNP, and BNP), atrial natriuretic peptide (e.g., proANP, NT-proANP, and ANP), troponin, C-reactive protein, creatinine, Blood Urea Nitrogen (BUN), liver function enzymes, albumin, and bacterial endotoxin. Additional non-limiting markers of a cardiovascular disease are described in U.S. Patent Application Publication Nos.: 2007/0248981; 2011/0053170; 2010/0009356; 2010/0055683; and 2009/0264779 (each of which is hereby incorporated by reference). Additional markers of a cardiovascular disease are known in the art.

Methods for determining the level of the above described markers of a cardiovascular disease are known in the art. Diagnostic tests for determining the level of several of these markers are commercially available. For example, diagnostic tests for determining the level of C-reactive protein (e.g., Exocell), B-type natriuretic peptide (e.g., Alpco Immunoassays), atrial natriuretic peptide (e.g., Cusabio Biotech Co., Ltd.), and cardiac troponin I (e.g., Calbiotech Inc.) are commercially available.

Additional Therapeutic Treatments

In any of the methods described herein, the subject can further be administered an additional therapeutic treatment (e.g., at least one therapeutic treatment in addition to exercise therapy). In some embodiments of the methods described herein, the subject can be receiving at least one therapeutic treatment at the time the exercise therapy begins. In some embodiments, a health care professional may adjust (e.g., increase or decrease) the dosage or frequency of administration of at least one therapeutic agent administered to the subject prior to the start of exercise therapy or at a time point during the exercise therapy. In some embodiments of the methods described herein, the efficacy of the exercise therapy allows for a decrease in the number of therapeutic agents or allows for a decrease in the dose or frequency of administration of one or more therapeutic agents to a subject having a cardiovascular disease.

Non-limiting examples of therapeutic treatment of a cardiovascular disease (in addition to exercise therapy) include the administration of one of more of the following agents: statins, anti-inflammatory agents, anti-thrombotic agents, anti-coagulants, anti-platelet agents, lipid-reducing agents, direct thrombin inhibitors, glycoprotein IIb/IIIa receptor inhibitors, calcium channel blockers, beta-adrenergic receptor blockers, cyclooxygenase-2 inhibitors, and renin-angiotensin-aldosterone system (RAAS) inhibitors.

Non-limiting examples of lipid-reducing agents that can be used to treat a cardiovascular disease in a subject (alone or in combination any other therapy, including exercise therapy) include: a statin, gemfibrozil, cholystyramine, colestipol, nicotinic acid, and probucol. Statins are molecules that are capable of inhibiting the activity of HMG-CoA reductase. Non-limiting examples of statins that can be administered to a subject having a cardiovascular disease (alone or in combination with any other therapy, including exercise therapy) include: atorvastatin, cirivastatin, fluvastatin, lovastatin, pitavastatin, pravastatin, rosuvastatin, and simvastatin. Additional examples of statins and other lipid-reducing agents are known in the art.

Non-limiting examples of anti-inflammatory agents that can be used to treat a cardiovascular disease in a subject (alone or in combination any other therapy, including exercise therapy) include: Alclofenac, Alclometasone Dipropionate, Algestone Acetonide, Alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Deflazacort, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lornoxicam, Loteprednol Etabonate, Meclofenamate Sodium, Meclofenamic Acid, Meclorisone Dibutyrate, Mefenamic Acid, Mesalamine, Meseclazone, Methylprednisolone Suleptanate, Morniflumate, Nabumetone, Naproxen, Naproxen Sodium, Naproxol, Nimazone, Olsalazine Sodium, Orgotein, Orpanoxin, Oxaprozin, Oxyphenbutazone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Salycilates, Sanguinarium Chloride, Seclazone, Sermetacin, Sudoxicam, Sulindac, Suprofen, Talmetacin, Talniflumate, Talosalate, Tebufelone, Tenidap, Tenidap Sodium, Tenoxicam, Tesicam, Tesimide, Tetrydamine, Tiopinac, Tixocortol Pivalate, Tolmetin, Tolmetin Sodium, Triclonide, Triflumidate, Zidometacin, Glucocorticoids, and Zomepirac Sodium. One preferred anti-inflammatory agent is aspirin. Additional examples of anti-inflammatory agents are known in the art.

Non-limiting examples of anti-thrombotic agents that can be used to treat a cardiovascular disease in a subject (alone or in combination with any other therapy, including exercise therapy) include: plasminogen proactivator, tissue plasminogen activator, Anisoylated Plasminogen-Streptokinase Activator Complex, Pro-Urokinase, (Pro-UK), rTPA (recombinant alteplase or activase), recombinant Pro-UK, Abbokinase, Eminase, Sreptase Anagrelide Hydrochloride, Bivalirudin, Dalteparin Sodium, Danaparoid Sodium, Dazoxiben Hydrochloride, Efegatran Sulfate, Enoxaparin Sodium, Ifetroban, Ifetroban Sodium, Tinzaparin Sodium, Retaplase, Trifenagrel, Warfarin, and Dextrans. Additional examples of anti-thrombotic agents are known in the art.

Non-limiting examples of anti-coagulants that can be used to treat a cardiovascular disease in a subject (alone or in combination with any other therapy, including exercise therapy) include: Ancrod, Anticoagulant Citrate Dextrose Solution, Anticoagulant Citrate Phosphate Dextrose Adenine Solution, Anticoagulant Citrate Phosphate Dextrose Solution, Anticoagulant Heparin Solution, Anticoagulant Sodium Citrate Solution, Ardeparin Sodium, Bivalirudin, Bromindione, Dalteparin Sodium, Desirudin, Dicumarol, Heparin Calcium, Heparin Sodium, Lyapolate Sodium, Nafamostat Mesylate, Phenprocoumon, Tinzaparin Sodium, and Warfarin Sodium. Additional examples of anti-coagulants are known in the art.

Non-limiting examples of anti-platelet agents that can be used to treat a cardiovascular disease in a subject (alone or in combination with any other therapy, including exercise therapy) include: Clopridogrel, Sulfinpyrazone, Aspirin, Dipyridamole, Clofibrate, Pyridinol Carbamate, Prostaglandin E, Glucagon, Antiserotonin drugs, Caffeine, Theophyllin Pentoxifyllin, Ticlopidine, and Anagrelide. Additional examples of anti-platelet agents are known in the art.

Non-limiting examples of direct thrombin inhibitors that can be used to treat a cardiovascular disease in a subject (alone or in combination with any other therapy, including exercise therapy) include: hirudin, hirugen, hirulog, agatroban, PPACK, and thrombin aptamers. Additional examples of thrombin inhibitors are known in the art.

Non-limiting examples of glycoprotein IIb/IIIb receptor inhibitors that can be used to treat a cardiovascular disease in a subject (alone or in combination with any other therapy, including exercise therapy) include: ReoPro (abcixamab), lamifiban, and tirofiban. Additional examples of glycoprotein IIb/IIIb receptor inhibitors are known in the art.

Non-limiting examples of calcium channel blockers that can be used to treat a cardiovascular disease in a subject (alone or in combination with any other therapy, including exercise therapy) include: dihydropyridines, such as nifedipine; phenyl alkyl amines, such as verapamil; and benzothiazepines, such as diltiazem. Additional non-limiting examples of calcium channel blockers include amrinone, amlodipine, bencyclane, felodipine, fendiline, flunarizine, isradipine, nicardipine, nimodipine, perhexilene, gallopamil, tiapamil, tiapamil analogues (such as 1993RO-11-2933), phenytoin, barbiturates, and the peptides dynorphin, omega-conotoxin, and omega-agatoxin, and the like and/or pharmaceutically acceptable salts thereof. Additional examples of calcium channel blockers are known in the art.

Non-limiting examples of beta-adrenergic receptor blockers that can be used to treat a cardiovascular disease in a subject (alone or in combination with any other therapy, including exercise therapy) include: atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitril HCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, and 7-(2-hydroxy-3-t-butylaminpropoxy) phthalide. The above beta-adrenergic receptor blockers can be used as isomeric mixtures, or in their respective levorotating or dextrorotating form. Additional examples of beta-adrenergic receptor blockers are known in the art.

Non-limiting examples of cyclooxygenase-2 inhibitors that can be used to treat a cardiovascular disease in a subject (alone or in combination with any other therapy, including exercise therapy) include those described in U.S. Pat. Nos. 5,474,995; 5,521,213; 5,536,752; 5,550,142; 5,552,422; 5,604,253; 5,604,260; 5,639,780; 5,677,318; 5,691,374; 5,698,584; 5,710,140; 5,733,909; 5,789,413; 5,817,700; 5,849,943; 5,861,419; 5,922,742; 5,925,631; 5,643,933; 5,474,995; and 5,543,297; WO 95/00501, and WO 95/18799 (each of which is incorporated herein by reference). Additional examples of cyclooxygenase-2 inhibitors are known in the art.

Renin-angiotensin-aldosterone system (RAAS) inhibitors can be used to treat a cardiovascular disease in a subject (alone or in combination with any other therapy, such as exercise therapy). RAAS inhibitors include agents that interfere with the function and synthesis or catabolism of angiotensin II. RAAS agents include, but are not limited to, angiotensin-converting enzyme (ACE) inhibitors, angiotensin II receptor blockers, agents that activate the catabolism of angiotensin II, agents that prevent the synthesis of angiotensin I (from which angiotensin II is ultimately derived), and aldosterone antagonists. The RAAS is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function. RAAS inhibitors are compounds that act to interfere with the production of angiotensin II from angiotensinogen or angiotensin I or interfere with the activity of angiotensin II. Such inhibitors are well known in the art and include compounds that act to inhibit the enzymes involved in the ultimate production of angiotensin II, including renin and ACE. They also include compounds that interfere with the activity of angiotensin II, once produced.

Angiotensin II receptor blockers include angiotensin II antagonists which interfere with the activity of angiotensin II by binding to angiotensin II receptors and interfere with their activity. Angiotensin II receptor blockers are well known and include peptide compounds and non-peptide compounds. Most angiotensin II receptor blockers are slightly modified congeners in which agonist activity is attenuated by replacement of phenylalanine in position 8 with some other amino acid. Examples of angiotensin II receptor blockers include: peptidic compounds (e.g., saralasin, [(San1)(Val5)(Ala8)] angiotensin-(1-8) octapeptide, and related analogs); N-substituted imidazole-2-one (U.S. Pat. No. 5,087,634); imidazole acetate derivatives, including 2-N-butyl-4-chloro-1-(2-chlorobenzile), imidazole-5-acetic acid (see, Long et al., J. Pharmacol. Exp. Ther. 247:1-7, 1988); 4, 5, 6, 7-tetrahydro-1H-imidazo [4, 5-c] pyridine-6-carboxylic acid, and analog derivatives thereof (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives, such as 1, 3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds, such as biphenyl-methyl substituted imidazoles (e.g., EP 253,310); N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide; SKF 108566 (E-alpha-2-[2-butyl-1-(carboxyphenyl)methyl] 1H-imidazole-5-yl [methylane]-2-thiophenepropanoic acid); Losartan; Remikirin; and A2 agonists.

Non-limiting examples of ACE inhibitors include acyl-mercapto and mercaptoalkanoyl prolines, such as captopril (U.S. Pat. No. 4,105,776) and zofenopril (U.S. Pat. No. 4,316,906); carboxyalkyl dipeptides, such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729); carboxyalkyl dipeptide mimics, such as cilazapril (U.S. Pat. No. 4,512,924) and benazapril (U.S. Pat. No. 4,410,520); and phosphinylalkanoyl prolines, such as fosinopril (U.S. Pat. No. 4,337,201) and trandolopril.

Additional non-limiting examples of RAAS inhibitors include: derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine, or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437) (each of which is incorporated by reference).

Additional examples of RAAS inhibitors include aldosterone antagonists. Non-limiting examples of aldosterone antagonists include: Spironolactone, Eplerenone, Canrenone (canrenoate potassium), Prorenone (prorenoate potassium), and Mexrenone (mexrenoate potassium).

EXAMPLES

The invention is further described in the following examples, which do not limit the scope of the invention described in the claims.

Example 1. Soluble ST2 Levels are Predictive of Mortality and Adverse Events in Heart Failure Patients Analysis was performed on the samples and data collected from 2331 heart failure patients enrolled in the HF-ACTION study. A total of 2329 of the patients underwent baseline exercise testing and were randomized to exercise therapy or normal clinical therapy. Of these patients, blood samples were collected from 912 patients representing both arms of the study, 453 were in the exercise arm and 459 were in the normal treatment arm. Nine hundred and ten of these patients had a sufficient sample size for soluble ST2 measurement. The median soluble ST2 level in this cohort was 23.7 ng/ml, and ranged from 2.2 ng/mL to 344.2 ng/ml. As in the previously published heart failure cohorts, soluble ST2 levels were predictive of death for the full duration of the follow-up period (up to 1460 days). The prognostic value of soluble ST2 levels for risk of death in heart failure patients during the entire follow-up period (up to 1460 days) is illustrated in FIG. 1. Patients in the highest soluble ST2 level group (soluble ST2 levels of greater than 28.6 ng/mL) have the greatest risk of mortality, with this risk presenting early in the follow-up period. The increased risk of mortality for those patients in the highest soluble ST2 level group is maintained throughout the entire follow-up period.

Figure 2:
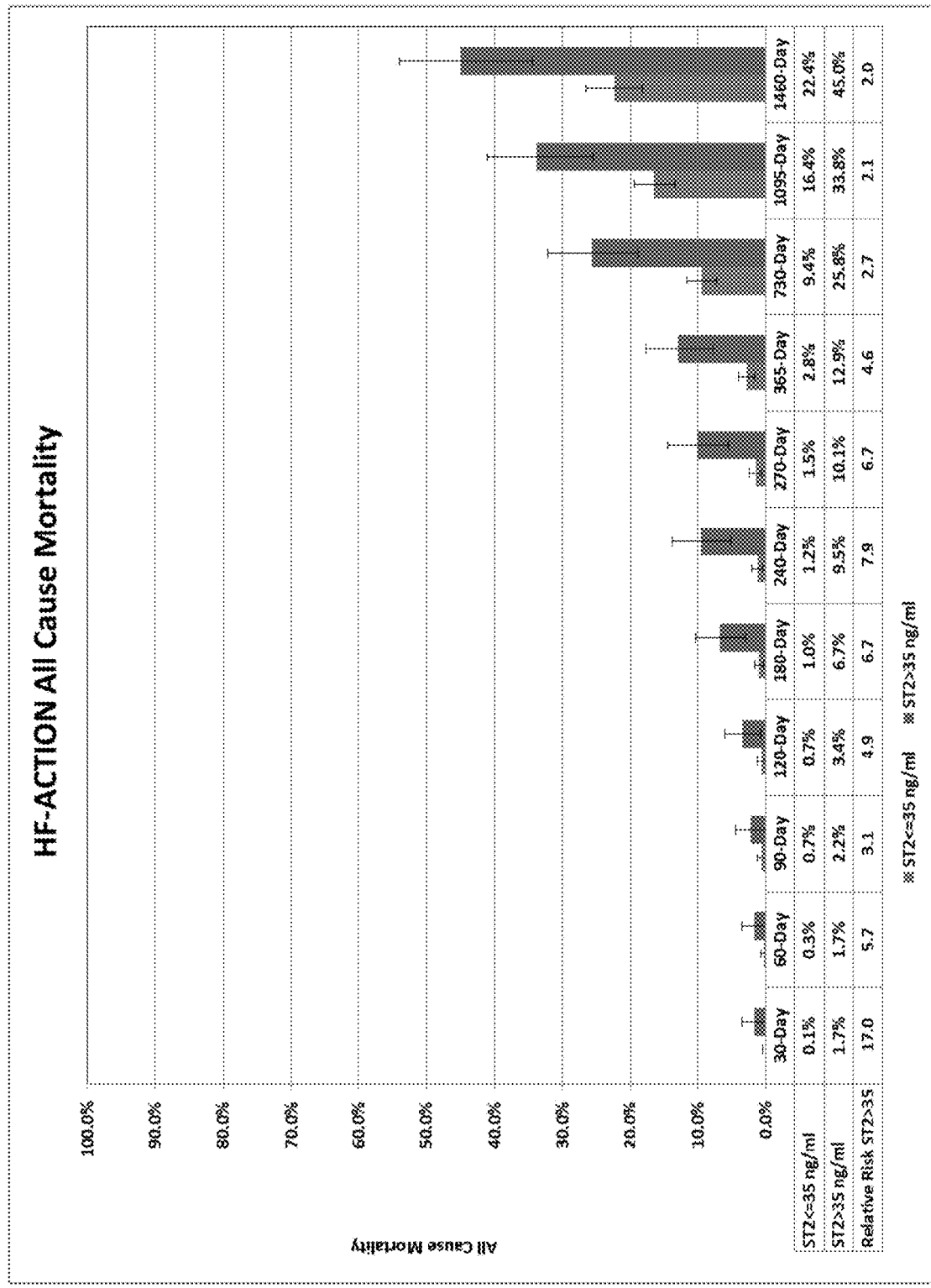
FIG. 2 is a graph and table showing the percentage of mortality in heart failure subjects over time. The percentage mortality data for heart failure subjects having a soluble ST2 level equal to or less than 35 ng/mL (left bar for each time point), or greater than 35 ng/mL (right bar for each time point) are shown. The table also shows the relative risk of mortality at each time point for subjects having a soluble ST2 level greater than 35 ng/mL compared to subjects having a soluble ST2 level less than or equal to 35 ng/mL.

The predictive strength of soluble ST2 levels was also assessed by Cox proportional hazards analysis, using soluble ST2 level as both a log (ln)-transformed continuous variable (HR 3.38, $p<0.0001$), as well as a dichotomous variable at a concentration of 35 ng/ml (HR 2.59, $p<0.0001$). FIG. 2 shows the surviving portion of heart failure patients over time for subjects having ST2 concentrations above or below a level of 35 ng/mL.

Figure 3:
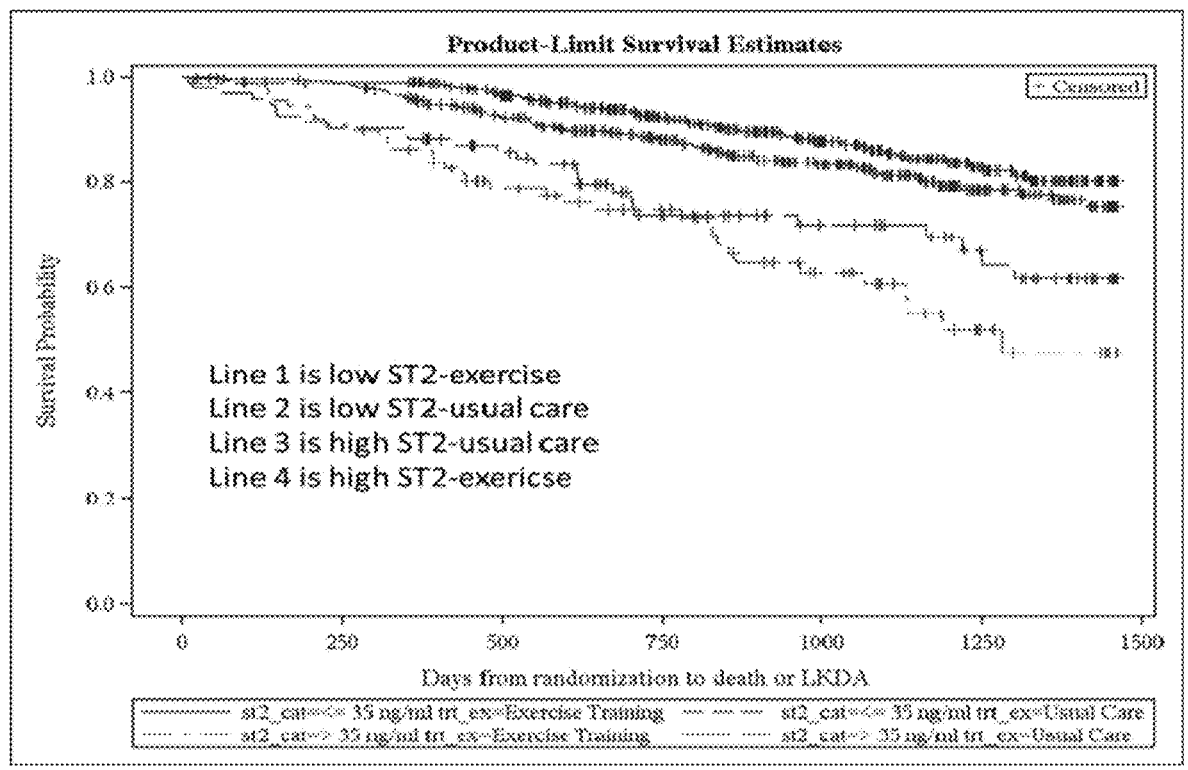
FIG. 3 is a Kaplan-Meier graph showing the surviving proportion of heart failure subjects over time within the identified groups. The survival data for subjects having a soluble ST2 level equal to or less than 35 ng/mL and performing an exercise treatment regimen (top line), subjects having a level of soluble ST2 greater than 35 ng/mL and not performing an exercise treatment regimen (second line from top), subject having a level of soluble ST2 greater than 35 ng/mL and not performing an exercise treatment regime (second line from bottom), and subjects having a level of soluble ST2 equal to or less than 35 ng/mL and performing an exercise treatment regime (bottom line) are shown.

Example 2. Subjects with Elevated Levels of Soluble ST2 Performing an Exercise Therapy Regime have an Increased Risk of Death As reported in O'Connor et al. (*JAMA* 301(14):1439-1450, 2009) there was a modest, but insignificant, decrease in mortality rate in heart failure patients who underwent exercise therapy relative to those who received standard care. An assessment of soluble ST2 levels in this cohort shows that the therapeutic efficacy of exercise therapy is different in patients having a high versus low level of soluble ST2, with more benefit, e.g., lower mortality rate, observed in heart failure patients with low soluble ST2 levels. This correlation is illustrated in a Kaplan-Meier analysis of the data from the following heart failure patient groups: patients having a level of soluble ST2 less than or equal to 35 ng/mL and performing an exercise therapy regime (line 1, top line); patients having a level of soluble ST2 less than or equal to 35 ng/nL and not performing an exercise therapy regime (line 2, second line from the top); patients having a level of soluble ST2 greater than 35 ng/mL and not performing an exercise therapy regime (line 3, second line from the bottom); and patients having a level of soluble ST2 greater than 35 ng/mL and performing an exercise therapy regime (line 4, bottom line) (FIG. 3). In both treatment arms (i.e., those performing an exercise therapy regime or those receiving standard care (not performing an exercise therapy regime)), heart failure patients with low soluble ST2 levels have better survival over the 4 year follow-up period than patients with elevated soluble ST2 levels. By 1 year, the patients with low soluble ST2 levels who performed an exercise therapy regime had a significantly lower mortality rate (~3%) compared to the usual care treatment group (not performing an exercise therapy regime), and this benefit persisted for the full 4-year follow-up period. Conversely, the data from heart failure patients with elevated soluble ST2 levels show no survival benefit from the performance of an exercise therapy regime out to 2 years of followup. After 2 years, there was an apparent adverse effect (increased mortality) of performing an exercise treatment regime in heart failure patients with elevated soluble ST2 levels compared to the usual care (not performing an exercise therapy regime) patients.

The ST2 analysis cutpoint of 35 ng/mL was selected by choosing a Presage ST2 Assay concentration value above the 90th and below the 95th percentile of the group. These reference values were subsequently confirmed to be consistent with an additional 3,450 subjects measured in a large observational population study, the Framingham Offspring Cohort (Wang et al. 2004) by showing that ST2 values are 32.9 ng/ml and 37.3 ng/ml at the 90th and 95th percentiles respectively, bracketing and confirming the selected 35 ng/ml value.

Figure 4:
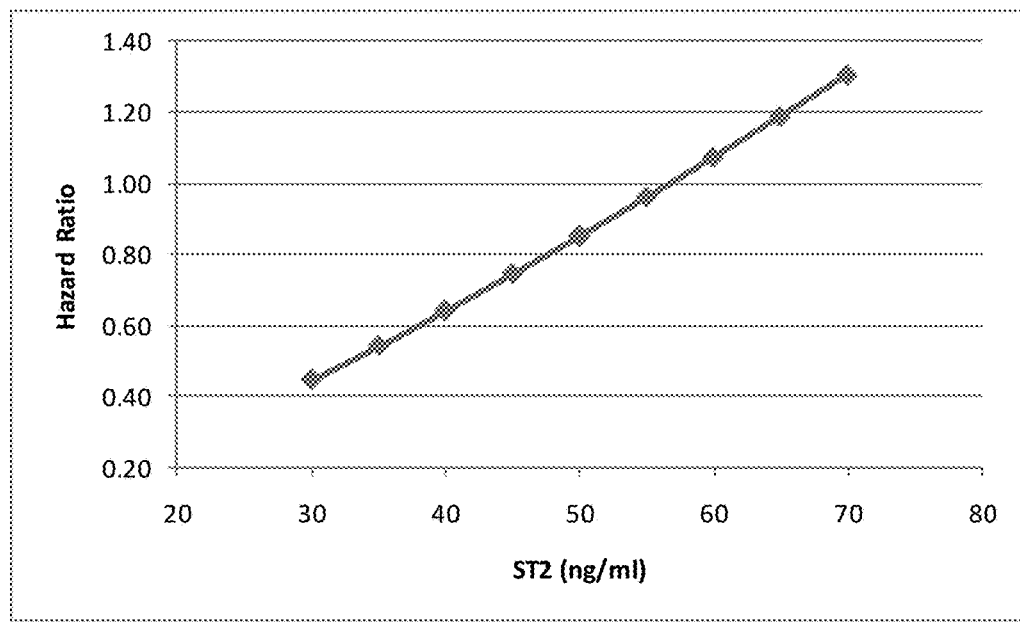
FIG. 4 is a graph of the hazard ratio for mortality within 1 year in heart failure subjects performing an exercise treatment regime compared to heart failure subjects not performing an exercise treatment regime having the different soluble ST2 levels shown.

The relationship between the mortality risk of performing an exercise therapy regime and soluble ST2 levels in heart failure patients is also illustrated in FIG. 4. The data in FIG. 4 show the calculated hazard ratio for mortality within 1 year in heart failure subjects performing an exercise treatment regime to heart failure subjects not performing an exercise treatment regime having different soluble ST2 levels. These data show that, as soluble ST2 levels increase there is a steady increase in the hazard ratio, reflecting worse survival, and that a level of soluble ST2 between 55 and 60 ng/mL has a hazard ratio of 1.0. These data indicated that heart failure patients with soluble ST2 levels below 55-60 ng/mL are likely to benefit from performing an exercise therapy regime, with greater benefit achieved at lower soluble ST2 levels. Heart failure patients with soluble ST2 levels above 55-60 ng/mL are not likely to achieve a therapeutic benefit from performing an exercise therapy regime and are at increased risk of experiencing an adverse outcome (e.g., mortality).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining whether a subject having heart failure should discontinue or continue exercise therapy, the method comprising:
   a) determining a level of soluble ST2 in a biological sample obtained from the subject at a first time point before or after the start of exercise therapy; and
   b) determining a level of soluble ST2 in a biological sample obtained from the subject undergoing exercise therapy at a second time point after the start of exercise therapy and after the first time point,
   wherein an elevation in the level of soluble ST2 in the biological sample at the second time point compared to the level of soluble ST2 in the biological sample at the first time point indicates that the subject should discontinue exercise therapy, and a decrease in the level of soluble ST2 in the biological sample at the second time point compared to the level of soluble ST2 in the biological sample at the first time point indicates that the subject should continue exercise therapy.

2. The method of claim 1, wherein the biological sample obtained from the subject at the first time point and the biological sample obtained from the subject at the second time point comprise blood or serum.

3. The method of claim 1, wherein the determining is performed using an antibody or an antibody fragment thereof that binds to soluble ST2.

4. The method of claim 1, wherein the subject is hypercholesterolemic, hypertriglyceridemic, hyperlidemic, a smoker, hypertensive, or has a body mass index of greater than 30.

5. The method of claim 1, further comprising determining a level of cardiac troponin I, B-type natriuretic peptide, atrial natriuretic peptide, or C-reactive protein in the biological sample obtained from the subject at the first time point or the biological sample obtained from the subject at the second time point.

6. The method of claim 1, wherein the subject is administered at least one therapeutic agent selected from the group consisting of: anti-inflammatory agents, anti-thrombotic agents, anti-coagulants, anti-platelet agents, lipid-reducing agents, direct thrombin inhibitors, glycoprotein IIb/IIIb receptor inhibitors, calcium channel blockers, beta-adrenergic receptor blockers, cyclooxygenase-2 inhibitors, and renin-angiotensin-aldosterone system (RAAS) inhibitors.

7. The method of claim 6, wherein the RAAS inhibitor is selected from the group consisting of: an angiotensin-converting enzyme inhibitor, an angiotensin II receptor blocker, and an aldosterone antagonist.

8. The method of claim 6, wherein the lipid-reducing agent is a statin.

\* \* \* \* \*

UNITED STATES PATENT AND TRADEMARK OFFICE
CERTIFICATE OF CORRECTION

PATENT NO. : 10,928,393 B2
APPLICATION NO. : 16/170870
DATED : February 23, 2021
INVENTOR(S) : James V. Snider and Robert W. Gerwien Page 1 of 1

It is certified that error appears in the above-identified patent and that said Letters Patent is hereby corrected as shown below:

In the Claims

Column 34, Line 63, Claim 4, delete "hyperlidemic," and insert -- hyperlipidemic, --, therefor.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*